(12) United States Patent
Fahrner et al.

(10) Patent No.: US 7,947,813 B2
(45) Date of Patent: May 24, 2011

(54) POLYELECTROLYTE PRECIPITATION AND PURIFICATION OF PROTEINS

(75) Inventors: Robert L. Fahrner, San Mateo, CA (US); Jayme Franklin, San Mateo, CA (US); Paul McDonald, San Francisco, CA (US); Thanmaya Peram, Campbell, CA (US); Vikram Sisodiya, San Jose, CA (US); Corazon Victa, Walnut Creek, CA (US)

(73) Assignee: Genentech, Inc., South San Francisco, CA (US)

( * ) Notice: Subject to any disclaimer, the term of this patent is extended or adjusted under 35 U.S.C. 154(b) by 499 days.

(21) Appl. No.: 11/972,010

(22) Filed: Jan. 10, 2008

(65) Prior Publication Data

US 2008/0193981 A1 Aug. 14, 2008

Related U.S. Application Data

(60) Provisional application No. 61/013,446, filed on Dec. 13, 2007, provisional application No. 60/886,068, filed on Jan. 22, 2007.

(51) Int. Cl.
C07K 1/22 (2006.01)
C07K 1/32 (2006.01)

(52) U.S. Cl. ............... 530/390.5; 530/413; 530/421

(58) Field of Classification Search .................. None
See application file for complete search history.

(56) References Cited

U.S. PATENT DOCUMENTS

| | | | |
|---|---|---|---|
| 3,252,961 | A | 5/1966 | Rodgers et al. |
| 4,055,469 | A | 10/1977 | Snoke et al. |
| 4,533,496 | A | 8/1985 | Lewis, Jr. et al. |
| 5,641,870 | A | 6/1997 | Rinderknecht et al. |
| 5,922,531 | A | 7/1999 | Dubin et al. |
| 6,265,542 | B1 | 7/2001 | Fahrner et al. |
| 6,797,814 | B2 | 9/2004 | Blank |
| 6,870,034 | B2 | 3/2005 | Breece et al. |
| 6,927,282 | B2 | 8/2005 | Chivers et al. |
| 7,026,453 | B2 | 4/2006 | Haj-Ahmad |
| 7,074,404 | B2 | 7/2006 | Basey et al. |
| 7,169,908 | B2 | 1/2007 | Lester et al. |
| 2005/0038231 | A1 | 2/2005 | Fahrner et al. |
| 2007/0193938 | A1 | 8/2007 | Yavorsky |
| 2009/0036651 | A1* | 2/2009 | Moya .......................... 530/351 |

FOREIGN PATENT DOCUMENTS

| WO | 2004/014942 A1 | 2/2004 |
|---|---|---|
| WO | 2004/092393 A1 | 10/2004 |

OTHER PUBLICATIONS

Sternberg, Biotechnology & Bioengineering, vol. XII, pp. 1-17, 1970.*
Carlsson et al., "Protein-polyelectrolyte cluster formation and redissolution: a Monte Carlo study" *J. Am. Chem. Soc.* (J. Am. Chem. Soc.) 125:3140-3149 (2003).
Carter-Franklin et al., "Fragments of protein A eluted during protein A affinity chromatography" *Journal of Chromatography*, 1161(1-2):105-111 (2007).
Cooper et al., "Polyelectrolyte-protein complexes" *Current Opin. in Colloid & Interface Science* 10:52-78 (2005).
Dainiak et al., "Production of Fab fragments of monoclonal antibodies using polyelectrolyte complexes" *Analytical Biochemistry* 277:58-66 (2000).
Dubin et al., "Protein Purification by Selective Phase Separation with Polyelectrolytes" *Separation and Purification Methods* 23(1):1-16 (1994).
Fahrner et al., "Expanded bed protein A affinity chromatography of a recombinant humanized monoclonal antibody: process development, operation, and comparison with a packed bed method" *Journal of Biotechnology* 75:273-280 (1999).
Fahrner et al., "Industrial Purification of Pharmaceutical Antibodies: Development, Operation, and Validation of Chromatography Processes" *Biotechnology & Genetic Engineering Reviews* 18:301-327 (2001).
Fahrner et al., "Performance comparison of protein A affinity-chromatography sorbents for purifying recombinant monoclonal antibodies" *Biotechnology and Applied Biochemistry* 30(2):121-128 (1999).
Follman et al., "Factorial screening of antibody purification processes using three chromatography steps without protein A" *Journal of Chromatography* 1024(1-2):79-85 (2004).
Knudsen et al., "Membrane ion-exchange chromatography for process-scale antibody purification" *Journal of Chromatography* 907(1-2):145-154 (2001).
Lazzareschi., "An effective, low cost wash buffer for the removal of host cell proteins from protein A affinity chromatography resin" (BIOT-151 Abstracts of Papers, 227th ACS National Meeting, Anaheim, CA, United States, Mar. 28-Apr. 1, 2004) pp. (1 page).
Mattison et al., "Micro- and Macro-phase Behavior in Protein-polyelectrolyte Complexes" *Macromol. Symp.* 140:53-76 (1999).
McDonald et al., "Selective precipitation using polyelectrolytes: A novel approach to the purification of monoclonal antibodies" (BIOT-440 Abstracts of Papers, 234th ACS National Meeting, Boston, MA, United States, Aug. 19-23, 2007) pp. (1 page).
Sternberg and Hershberger, "Separation of Proteins with Polyacrylic Acids" *Biochem et Biophys. Acta* 342:195-206 (1974).
Victa et al., "Mechanisms of protein A leaching" (BIOT-334 Abstracts of Papers, 234th ACS National Meeting, Boston, MA, United States, Aug. 19-23, 2007) pp. (1 page).
Wang et al., "Protein Separation via Polyelectrolyte Coacervation: Selectivity and Efficiency" *Biotechnol. Prog.* 12:356-362 (1996).
Riske et al., "The use of chitosan as a flocculant in mammalian cell culture dramatically improves clarification throughput without adversely impacting monoclonal antibody recovery" *Journal of Biotechnology* 128:813-823 (2007).
Kozhevnikov, "Catalysis by Heteropoly Acids and Multicomponent Polyoxometalates in Liquid-Phase Reactions" *Chem. Rev.* 98:171-198 (1998).
Mattiasson et al., "Smart Polymers and Protein Purification" *Polym.-Plast. Technol. Eng.* 37(3):303-308 (1998).
McDonald et al., "Selective Antibody Precipitation Using Polyelectrolytes: A Novel Approach to the Purification of Monoclonal Antibodies" *Biotechnology and Bioengineering* 102(4):1141-1151 (Mar. 1, 2009).
Misono et al., "Heteropolyacids. Versatile green catalysts usable in a variety of reaction media" *Pure Appl. Chem.* 72(7):1305-1311 (2000).

* cited by examiner

*Primary Examiner* — David A Saunders
(74) *Attorney, Agent, or Firm* — Alex Andrus; Genentech, Inc.

(57) ABSTRACT

Methods are presented for isolating and purifying proteins by adding a polyelectrolyte to a cell culture fluid, such as a harvested cell culture fluid, and precipitating a protein-polyelectrolyte complex or a complex of impurities and the polyelectrolyte.

15 Claims, 24 Drawing Sheets

| | Load Density (mg/ml) | Yield % | CHOP (ng/mg) | Protein A (ng/mg) | Aggregate (%) | Monomer (%) | Fragment (%) | Insulin (ng/mg) | DNA pg/mg | Gentamicin (ng/mg) |
|---|---|---|---|---|---|---|---|---|---|---|
| HCCF | N/A | N/A | 234276 | N/A | N/D | N/D | N/D | 2.410 | 2730769 | 25460 |
| a) HCCF processed across Protein A | | | | | | | | | | |
| Protein A | 14 | 95 | 1105 | 23 | 0.80 | 98.92 | 0.27 | 0.002 | 198 | 9 |
| SP SFF | 40 | 95 | 199 | <2 | 0.82 | 98.99 | 0.19 | <0.034 | <0.18 | 0.26 |
| QSFF | 40 | 96 | <0.7 | <2 | 0.71 | 99.28 | 0.01 | <0.064 | <0.34 | 0.24 |
| Protein A | 14 | 95 | 1105 | 23 | 0.80 | 98.92 | 0.27 | 0.002 | 198 | 9 |
| QSFF | 40 | 97 | 3.9 | 23 | 0.64 | 99.11 | 0.25 | <0.051 | <0.27 | 5 |
| Protein A | 14 | | 1105 | 23 | 0.80 | 98.92 | 0.27 | 0.002 | 198 | 9 |
| PVS Precipitation pH 7 * | N/A | 100 | 244 | 4 | 0.74 | 99.21 | 0.04 | <0.064 | ND | 1.26 |
| QSFF | 40 | 92 | 1.1 | 2 | 0.68 | 99.29 | 0.03 | <0.080 | <0.42 | 1.29 |
| b) HCCF processed across SPSFF | | | | | | | | | | |
| SP SFF | 10 | 82 | 4252 | N/A | 0.34 | 90.42 | 9.24 | <0.086 | 0.55 | 146 |
| QSFF | 40 | 100 | 71 | N/A | 0.28 | 90.99 | 8.73 | <0.154 | 1.37 | 170 |
| SP SFF | 10 | 82 | 4252 | N/A | 0.34 | 90.42 | 9.24 | <0.086 | 0.55 | 146 |
| PVS Precipitation pH 7 * | N/A | 86 | 190 | N/A | 0.61 | 95.78 | 3.61 | <0.155 | ND | 8 |
| Q SFF | 40 | 95 | 4.1 | N/A | 0.51 | 95.98 | 3.51 | <0.177 | 0.94 | 8 |
| c) PVS Precipitation of HCCF | | | | | | | | | | |
| PVS Precipitation pH 5 * | N/A | 88 | 92854 | N/A | 1.75 | 95.93 | 2.32 | 2.077 | ND | 4484 |
| QSFF | 37 | 90 | 1589 | N/A | 0.21 | 99.30 | 0.49 | 1.934 | 2.05 | 2454 |
| SP SFF | 35 | 95 | 33 | N/A | 0.50 | 94.35 | 5.15 | <0.042 | <0.22 | 13 |
| PVS Precipitation pH 7 * | N/A | 82 | 27422 | N/A | 3.60 | 95.93 | 0.47 | 0.009 | ND | 2014 |
| Q SFF | 40 | 95 | 361 | N/A | 1.19 | 98.81 | 0.00 | <0.192 | 4.35 | 1158 |
| SP SFF | 40 | 102 | 18 | N/A | 0.99 | 98.80 | 0.21 | <0.033 | <0.18 | 4 |

Figure 11

POLYELECTROLYTE PRECIPITATION AND PURIFICATION OF PROTEINS

CROSS REFERENCE TO RELATED APPLICATIONS

This non-provisional application filed under 37 CFR §1.53 (b), claims the benefit under 35 USC §119(e) of U.S. Provisional Application Ser. No. 60/886,068 filed on 22 Jan. 2007, and U.S. Provisional Application Ser. No. 61/013,446 filed on 13 Dec. 2007 which are incorporated by reference in entirety.

FIELD OF THE INVENTION

The invention relates to methods for purifying proteins.

BACKGROUND OF THE INVENTION

The large-scale, economic purification of proteins is increasingly an important problem for the biotechnology industry. Generally, proteins are produced by cell culture, using either mammalian or bacterial cell lines engineered to produce the protein of interest by insertion of a recombinant plasmid containing the gene for that protein. Since the cell lines used are living organisms, they must be fed with a complex growth medium, containing sugars, amino acids, and growth factors, usually supplied from preparations of animal serum. Separation of the desired protein from the mixture of compounds fed to the cells and from the by-products of the cells themselves to a purity sufficient for use as a human therapeutic poses a formidable challenge.

Recombinant therapeutic proteins are commonly produced in several mammalian host cell lines including murine myeloma NS0 and Chinese Hamster Ovary (CHO) cells (Anderson, D. C and Krummen, L. (2002) Curr. Opin. Biotech. 13: 117-123; Chu, L. and Robinson, D. K. (2001) Curr. Opin. Biotechnol. 12:180-187). Each cell line has advantages and disadvantages in terms of productivity and the characteristics of the proteins produced by the cells. Choices of commercial production cell lines often balance the need for high productivity with the ability to deliver the product quality attributes required of a given product. One important class of therapeutic recombinant proteins which often require high titer processes are monoclonal antibodies. Some monoclonal antibodies need effector functions, mediated through the Fc region, to elicit their biological functions. An example is rituximab (RITUXAN®, Genentech, Inc. and Biogen-Idec), a chimeric monoclonal antibody which binds to cell surface CD-20 and results in B-cell depletion (Cartron et al (2002) Blood 99: 754-758; Idusogie et al (2000) J. Immunol. 164: 4178-4184). Other antibodies, such as bevacizumab (AVASTIN™, Genentech, Inc.), a humanized anti-VEGF (vascular endothelial growth factor) antibody, do not require Fc effector functions for their activity.

Advances in fermentation and cell culture techniques have greatly increased the titers of target proteins in culture fluid. This increase in upstream efficiency has led to a bottleneck in downstream processing at the cell-harvest stage. Cell harvesting, or clarification of the harvested cell culture fluid, is an important process in nearly all downstream purifications of biotech-based products. When the product is internal to the cells, cell harvesting is used to decrease the liquid volume of cells to be processed in the product extraction steps. When the product is extracellular, cell harvesting is used to separate the product from the cells and cellular debris, for example, the isolation of an extracellular antibody from mammalian cell culture (Anthony S. Lubiniecki, Ed. (1990) Large-Scale Mammalian Cell Culture Technology, Marcel Dekker; Hansjoerg Hauser, Roland Wagner, Eds. (1997) Mammalian Cell Biotechnology in Protein Production, Walter Gruyter Publishing).

Procedures for purification of proteins from cell debris initially depend on the site of expression of the protein. Some proteins can be caused to be secreted directly from the cell into the surrounding growth media; others are made intracellularly. For the latter proteins, the first step of a purification process involves lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. The same problem arises, although on a smaller scale, with directly secreted proteins due to the natural death of cells and release of intracellular host cell proteins in the course of the protein production run.

During the purification of therapeutic antibodies, impurities including host cell proteins, product variants, host cell DNA, small molecules, process related contaminants, endotoxins and viral particles must be removed (Fahrner, R. L. et al (2001) Biotechnol. Genet. Eng. Rev. 18:301-327). The purification techniques used must be scaleable, efficient, cost-effective, reliable, and meet the rigorous purity requirements of the final product. Current purification techniques typically involve multiple chromatographic separations employing orthogonal modes of separation. A typical process might include some of the following steps: precipitation (U.S. Pat. No. 7,169,908), dialysis, electrophoresis, ultrafiltration, affinity chromatography, cation exchange chromatography, anion exchange chromatography and/or hydrophobic interaction chromatography. Conventional column chromatography steps are effective and reliable, but generally have low product throughput (kg processed/h). As monoclonal antibodies become more widely used, more efficient process-scale production is necessary.

Chromatography techniques exploit the chemical and physical properties of proteins to achieve a high degree of purification. These chemical and physical properties typically include size, isoelectric point, charge distribution, hydrophobic sites and affinity for ligands (Janson, J. C. and L. Ryden (eds.). (1989) *Protein Purification: Principles, High Resolution Methods and Applications*. VCH Publishers, Inc., New York). The various separation modes of chromatography include: ion-exchange, chromatofocusing, gel filtration (size exclusion), hydrophobic interaction, reverse phase, and affinity chromatography. Ion-exchange chromatography (IEX), including anion-exchange and cation-exchange chromatography separates analytes (e.g. proteins) by differences of their net surface charges. IEX is a primary tool for the separation of expressed proteins from cellular debris and other impurities. Today, IEX is one of the most frequently used techniques for purification of proteins, peptides, nucleic acids and other charged biomolecules, offering high resolution and group separations with high loading capacity. The technique is capable of separating molecular species that have only minor differences in their charge properties, for example two proteins differing by one charged amino acid. These features make IEX well suited for capture, intermediate purification or polishing steps in a purification protocol and the technique is used from microscale purification and analysis through to purification of kilograms of product.

Chromatography techniques are reliable but capacity and throughput can be problematic for large scale applications.

Conventional column chromatography steps are effective and reliable, but generally have low product throughput (kg processed/h). As recombinant proteins become more widely used, more efficient process-scale production is necessary. The throughput of a chromatography step is typically limited by the capacity of the chromatography resin for the protein of interest. With increased protein load to the column, resolution of the protein of interest from impurities often decreases.

Polyelectrolytes are known to form complexes with proteins which take the forms of soluble complexes (Dellacherie, E. (1991) Am. Chem. Soc., Div. Polym. Chem. Prepr. 32(1): 602), amorphous precipitates (Mattiasson et al (1998) Polym. Plast. Technol. Eng. 37(3):303-308; Clark et al (1987) Biotech. Progress 3(4):241; Fisher et al (1988) Biotechnol. Bioeng. 32:777; Shieh et al (1991) Am. Chem. Soc., Div. Polym. Chem. Prepr. 32(1)606; Sternberg et al (1974) Biochimica et Biophysica Acta 342:195-206; WO 2004/014942), or coacervates (Wang et al (1996) Biotechnol. Prog. 12:356-362; Veis, A. (1991) Am. Chem. Soc. Div. Polym. Chem. Prepr. 32(1) 596). Papain proteolysis of monoclonal antibodies in the presence of antigen-polycation (polymethacrylic acid) gives Fab fragments (Dainiak et al (2000) Analytical Biochem. 277:58-66).

Protein-polyelectrolyte complexes coacervate, i.e. separate into two distinct liquid phases where the coacervate phase contains most of the complex and the other phase is the equilibrium phase (Burgess, D. J. "Complex Coacervation: Microcapsule Formation" in Macromolecular Complexes in Chemistry and Biology, Dubin, P. L., et al Eds. (1994) Springer-Verlag, Berlin; Dubin et al (1994) Sep. Purif. Methods 23:1-16). Polyelectrolyte coacervation of proteins is a complicated process and is not useful for a broad range of proteins. The intermolecular associations in protein-polyelectrolyte complexes are due to electrostatic interactions, hydrogen bonds and hydrophobic forces (Cooper et al (2005) Current Opinion in Colloid & Interface Science 10:52-78; Mattison et al (1999) Macromol. Symp. 140:53-76). While it is known that addition of a polyelectrolyte to a protein solution can lead to the formation of protein-polyelectrolyte complexes and larger clusters and eventually to a coacervate and/or precipitation, the reverse process may appear upon further addition of polyelectrolyte whereby redissolution of protein occurs, defeating the attempt at protein isolation or purification (Carlsson et al (2003) J. Am. Chem. Soc. 125:3140-3149). Precipitation of proteins using polyelectrolytes may provide a cost-effective alternative to chromatography separation. Using this technique, it may be possible to exploit the functional chemistry of chromatographic techniques to achieve a similar level of protein purification in solution. In particular, the throughput of the precipitation step would no longer be limited by the capacity of a particular chromatography resin.

SUMMARY OF THE INVENTION

The invention provides methods relating to the isolation and purification of proteins derived from cell culture fluids.

One aspect of the invention is a protein purification process by precipitation of a protein with a polyelectrolyte, such as a polyanion polyelectrolyte.

The invention also provides a protein purification process by precipitation of cell culture fluid impurities with a polycation polyelectrolyte. The precipitation step may be followed by cation exchange chromatography, anion exchange chromatography, and other precipitation steps.

Methods of the invention include a non affinity process for the purification of an antibody One aspect of the invention is a method of purifying antibodies comprising:

(a) adjusting the acidity or salt concentration of a mixture containing an antibody wherein the antibody is derived from a harvested cell culture fluid;

(b) adding a negatively charged polyelectrolyte whereby a protein-polyelectrolyte precipitate is formed;

(c) separating the protein-polyelectrolyte precipitate from impurities selected from protein aggregates, protein fragments, host cell proteins, insulin, gentamicin, DNA, and leached protein A;

(d) isolating the protein-polyelectrolyte precipitate; and (e) resuspending the protein-polyelectrolyte precipitate in an aqueous solution.

Another aspect of the invention is a method of purifying antibodies comprising:

(a) adjusting the acidity or salt concentration of a mixture containing an antibody wherein the antibody is derived from a cell culture fluid;

(b) adding a positively charged, polycation polyelectrolyte to the mixture whereby a precipitate is formed comprising the positively charged, polycation polyelectrolyte and impurities selected from protein aggregates, protein fragments, host cell proteins, insulin, gentamicin and DNA; and (c) separating the precipitate from the mixture comprising the antibody.

BRIEF DESCRIPTION OF THE DRAWINGS

FIG. 11 shows a table of summary downstream processing results for anti-CD20 rhuMab 2H7: (a) HCCF processed across Protein A; (b) HCCF processed across SPSFF; (c) PVS precipitation of HCCF.

DETAILED DESCRIPTION OF EXEMPLARY EMBODIMENTS

Figure 1:
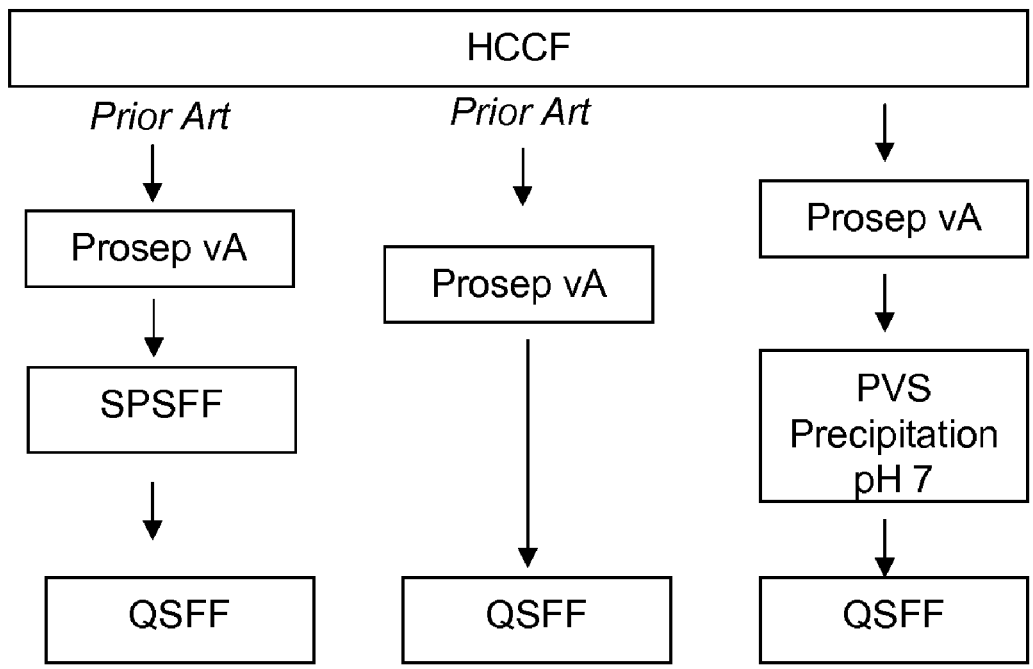
FIG. 1 shows process steps for the purification of protein A pool purified from harvested cell culture fluid (HCCF) followed by: left column—cation exchange chromatography (Sepharose™ fast flow, SPSFF) then anion exchange chromatography (QSFF); middle column—QSFF; or right column—polyvinylsulfonic acid (PVS) precipitation at pH 7 then QSFF.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

DEFINITIONS

Unless stated otherwise, the following terms and phrases as used herein are intended to have the following meanings:

The term "harvested cell culture fluid", also denoted as HCCF, means prokaryotic or eukaryotic cell culture fluid from which the cells have been removed, by means including centrifugation or filtration. Cell culture is the process by which either prokaryotic or eukaryotic cells are grown under controlled conditions. The term "cell culture" refers to the culturing of cells derived from multicellular eukaryotes, including animal cells or monocellular prokaryotes, including bacteria and yeast. Eukaryotic cell cultures include mammalian cells such as Chinese Hamster Ovary cells, hybridomas, and insect cells. With an appropriate cell culture vessel, secreted proteins can be obtained from anchorage dependent cells or suspension cell lines. Mammalian cell cultures include Chinese Hamster Ovary (CHO) cells.

The term "microbial fermentation" means cell culture of bacteria or yeast which is genetically engineered to produce chemicals such as proteins. Fermentation is used to propagate cloned bacteria and yeast as well as other microorganisms and produce proteins of value. The cell productivity and growth of these organisms are maximized by supplying particular growth media and controlling and various environmental factors (such as pH, temperature, and aeration). Bacterial fermentation fluid may be derived from E. Coli.

The term "antibody" herein is used in the broadest sense and specifically covers monoclonal antibodies, polyclonal antibodies, multispecific antibodies (e.g., bispecific antibodies), and antibody fragments, so long as they exhibit the desired biological activity. Antibodies may be murine, human, humanized, chimeric, or derived from other species.

An antibody is a protein generated by the immune system that is capable of recognizing and binding to a specific antigen. (Janeway, et al (2001) "Immunobiology", 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody.

The term "antibody," as used herein, also refers to a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

"Antibody fragments" comprise a portion of a full length antibody, generally the antigen binding or variable region thereof. Examples of antibody fragments include Fab, Fab', $F(ab')_2$, and Fv fragments; diabodies; linear antibodies; fragments produced by a Fab expression library, anti-idiotypic (anti-Id) antibodies, CDR (complementary determining region), ECD (extracellular domain), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature 256:495, or may be made by recombinant DNA methods (U.S. Pat. No. 4,816,567). The "monoclonal antibodies" may also be isolated from phage antibody libraries using the techniques described for example in Clackson et al (1991) Nature, 352:624-628; Marks et al (1991) J. Mol. Biol., 222: 581-597.

Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (MAb) to an antigen-of-interest can be prepared by using any technique known in the art which provides for the production of antibody molecules by continuous cell lines in culture. These include, but are not limited to, the hybridoma technique originally described by Köhler and Milstein (1975) Nature 256: 495-497), the human B cell hybridoma technique (Kozbor et al (1983) Immunology Today 4:72), and the EBV-hybridoma technique (Cole et al (1985) in Monoclonal Antibodies and Cancer Therapy, Alan R. Liss, Inc., pp. 77-96). Such antibodies may be of any immunoglobulin class including IgG, IgM, IgE, IgA, and IgD and any subclass thereof. The hybridoma producing the MAbs of use in this invention may be cultivated in vitro or in vivo.

Therapeutic monoclonal antibodies useful for the methods of the invention include trastuzumab (HERCEPTIN®, Genentech, Inc., Carter et al (1992) Proc. Natl. Acad. Sci. U.S.A., 89:4285-4289; U.S. Pat. No. 5,725,856); anti-CD20 antibodies such as chimeric anti-CD20 "C2B8" (U.S. Pat. No. 5,736,137); rituximab (RITUXAN®), ocrelizumab, a chimeric or humanized variant of the 2H7 antibody (U.S. Pat. No. 5,721,108; WO 04/056312) or tositumomab (BEXXAR®); anti-IL-8 (St John et al (1993) Chest, 103:932, and WO 95/23865); anti-VEGF antibodies including humanized and/or affinity matured anti-VEGF antibodies such as the humanized anti-VEGF antibody huA4.6.1 bevacizumab (AVASTIN®, Genentech, Inc., Kim et al (1992) Growth Factors 7:53-64, WO 96/30046, WO 98/45331); anti-PSCA antibodies (WO 01/40309); anti-CD40 antibodies, including S2C6 and humanized variants thereof (WO 00/75348); anti-CD11a (U.S. Pat. No. 5,622,700; WO 98/23761; Steppe et al (1991) Transplant Intl. 4:3-7; Hourmant et al (1994) Transplantation 58:377-380); anti-IgE (Presta et al (1993) J. Immunol. 151:2623-2632; WO 95/19181); anti-CD18 (U.S. Pat. No. 5,622,700; WO 97/26912); anti-IgE, including E25, E26 and E27 (U.S. Pat. Nos. 5,714,338; 5,091,313; WO 93/04173; U.S. Pat. No. 5,714,338); anti-Apo-2 receptor antibody (WO 98/51793); anti-TNF-alpha antibodies including cA2 (REMICADE®), CDP571 and MAK-195 (U.S. Pat. No. 5,672,347; Lorenz et al (1996) J. Immunol. 156(4):1646-1653; Dhainaut et al (1995) Crit. Care Med. 23(9):1461-1469); anti-Tissue Factor (TF) (EP 0 420 937 B1); anti-human alpha 4 beta 7 integrin (WO 98/06248); anti-EGFR, chimerized or humanized 225 antibody (WO 96/40210); anti-CD3 antibodies such as OKT3 (U.S. Pat. No. 4,515,893); anti-CD25 or anti-tac antibodies such as CHI-621 SIMULECT® and ZENAPAX® (U.S. Pat. No. 5,693,762); anti-CD4 antibodies such as the cM-7412 antibody (Choy et al (1996) Arthritis Rheum 39(1):52-56); anti-CD52 antibodies such as CAMPATH-1H (Riechmann et al (1988) Nature 332:323-337); anti-Fc receptor antibodies such as the M22 antibody directed against Fc gamma RI as in Graziano et al (1995) J. Immunol. 155(10):4996-5002; anti-carcinoembryonic antigen (CEA) antibodies such as hMN-14 (Sharkey et al (1995) Cancer Res. 55(23Suppl): 5935s-5945s; antibodies directed against breast epithelial cells including huBrE-3, hu-Mc 3 and CHL6 (Ceriani et al (1995) Cancer Res. 55(23): 5852s-5856s; and Richman et al (1995) Cancer Res. 55(23 Supp): 5916s-5920s); antibodies that bind to colon carcinoma cells such as C242 (Litton et al (1996) Eur J. Immunol. 26(1):1-9); anti-CD38 antibodies, e.g. AT 13/5 (Ellis et al (1995) J. Immunol. 155(2):925-937); anti-CD33 antibodies such as Hu M195 (Jurcic et al (1995) Cancer Res 55(23 Suppl):5908s-5910s and CMA-676 or CDP771; anti-CD22 antibodies such as LL2 or LymphoCide (Juweid et al (1995) Cancer Res 55(23 Suppl):5899s-5907s); anti-EpCAM antibodies such as 17-1A (PANOREX®); anti-GpIIb/IIIa antibodies such as abciximab or c7E3 Fab (REOPRO®); anti-RSV antibodies such as MEDI-493 (SYNAGIS®); anti-CMV antibodies such as PROTOVIR®); anti-HIV antibodies such as PRO542; anti-hepatitis antibodies such as the anti-Hep B antibody OSTAVIR®); anti-CA 125 antibody OvaRex; anti-idiotypic GD3 epitope antibody BEC2; anti-alpha v beta3 antibody VITAXIN®; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10 and the anti-HLA DR antibody Oncolym (Lym-1).

Useful monoclonal antibodies include, but are not limited to, human monoclonal antibodies, humanized monoclonal antibodies, antibody fragments, or chimeric human-mouse (or other species) monoclonal antibodies. Human monoclonal antibodies may be made by any of numerous techniques known in the art (Teng et al (1983) Proc. Natl. Acad. Sci. U.S.A. 80:7308-7312; Kozbor et al (1983) Immunology Today 4:72-79; and Olsson et al (1982) Methods in Enzymology 92:3-16).

The antibody can also be a bispecific antibody. Bispecific antibodies may have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (WO 94/04690; Suresh et al (1986) Methods in Enzymology, 121:210; Rodrigues et al (1993) J. of Immunology 151:6954-6961; Carter et al (1992) Bio/Technology 10:163-167; Carter et al (1995) J. of Hematotherapy 4:463-470; Merchant et al (1998) Nature Biotechnology 16:677-681. Methods for making bispecific antibodies are known in the art (Milstein et al (1983) Nature 305:537-539; WO 93/08829; Traunecker et al (1991) EMBO J. 10:3655-3659. Using such techniques, bispecific antibodies can be prepared for conjugation as ADC in the treatment or prevention of disease as defined herein.

According to a different approach, antibody variable domains with the desired binding specificities (antibody-antigen combining sites) are fused to immunoglobulin constant domain sequences. The fusion protein may be with an immunoglobulin heavy chain constant domain, comprising at least part of the hinge, $C_H2$, and $C_H3$ regions. The first heavy-chain constant region ($C_H1$) may contain the site necessary for light chain binding, present in at least one of the fusion proteins. Nucleic acids with sequences encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

Hybrid or bifunctional antibodies can be derived either biologically, i.e., by cell fusion techniques, or chemically, especially with cross-linking agents or disulfide-bridge forming reagents, and may comprise whole antibodies or fragments thereof (EP 105360; WO 83/03679; EP 217577).

The antibody can be a functionally active fragment, derivative or analog of an antibody that immunospecifically binds to cancer cell antigens, viral antigens, or microbial antigens or other antibodies bound to tumor cells or matrix. In this regard, "functionally active" means that the fragment, derivative or analog is able to elicit anti-anti-idiotype antibodies that recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art, e.g. the BIA core assay (Kabat et al, (1991) in *Sequences of Proteins of Immunological Interest*, Fifth Edition, National Institute of Health, Bethesda, Md.; Kabat et al (1980) J. of Immunology 125(3):961-969).

Other useful antibodies include fragments of antibodies such as, but not limited to, F(ab')2 fragments, which contain the variable region, the light chain constant region and the CH1 domain of the heavy chain can be produced by pepsin digestion of the antibody molecule, and Fab fragments, which can be generated by reducing the disulfide bridges of the F(ab')2 fragments. Other useful antibodies are heavy chain and light chain dimers of antibodies, or any minimal fragment thereof such as Fvs or single chain antibodies (SCAs) (e.g., as described in U.S. Pat. No. 4,946,778; Bird (1988) Science 242:423-42; Huston et al., (1988) Proc. Natl. Acad. Sci. U.S.A. 85:5879-5883; and Ward et al (1989) Nature 334:544-54), or any other molecule with the same specificity as the antibody.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. U.S.A., 81:6851-6855). A chimeric antibody is a molecule in which different portions are derived from different animal species, such as those having a variable region derived from a murine monoclonal and human immunoglobulin constant regions (U.S. Pat. Nos. 4,816,567; 4,816,397). Chimeric antibodies include "primatized" antibodies comprising variable domain antigen-binding sequences derived from a non-human primate (e.g., Old World Monkey, Ape etc) and human constant region sequences.

Chimeric and humanized monoclonal antibodies, comprising both human and non-human portions, can be made using standard recombinant DNA techniques (WO 87/02671; EP 184,187; EP 171496; EP 173494; WO 86/01533; U.S. Pat. No. 4,816,567; EP 12023; Berter et al (1988) Science 240:

1041-1043; Liu et al (1987) Proc. Natl. Acad. Sci. U.S.A. 84:3439-3443; Liu et al (1987) J. Immunol. 139:3521-3526; Sun et al (1987) Proc. Natl. Acad. Sci. U.S.A. 84:214-218; Nishimura et al (1987) Cancer. Res. 47:999-1005; Wood et al (1985) Nature 314:446-449; and Shaw et al (1988) J. Natl. Cancer Inst. 80: 1553-1559; Morrison (1985) Science 229: 1202-1207; Oi et al (1986) BioTechniques 4: 214; U.S. Pat. No. 5,225,539; Jones et al (1986) Nature 321:552-525; Verhoeyan et al (1988) Science 239:1534; and Beidler et al (1988) J. Immunol. 141:4053-4060; each of which is incorporated herein by reference in its entirety.

Completely human antibodies can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995) Int. Rev. Immunol. 13:65-93; U.S. Pat. Nos. 5,625,126; 5,633,425; 5,569,825; 5,661,016; 5,545,806). Other human antibodies can be obtained from commercial sources, for example, Abgenix, Inc. (Freemont, Calif.) and Genpharm (San Jose, Calif.).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al (1994) Biotechnology 12:899-903). Human antibodies can also be produced using various techniques known in the art, including phage display libraries (Hoogenboom and Winter, J. Mol. Biol. 227:381 (1991); Marks et al (1991) J. Mol. Biol. 222:581).

The antibody may be a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, such as at least 10, 20 or 50 amino acid portion of the protein) that is not the antibody. The antibody or fragment thereof may be covalently linked to the other protein at the N-terminus of the constant domain.

Antibodies include analogs and derivatives that are either modified, i.e., by the covalent attachment of any type of molecule as long as such covalent attachment permits the antibody to retain its antigen binding immunospecificity. For example, but not by way of limitation, the derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques, including, but not limited to specific chemical cleavage, acetylation, formylation, metabolic synthesis in the presence of tunicamycin, etc. Additionally, the analog or derivative can contain one or more unnatural amino acids.

Examples of CD20 antibodies include: "C2B8," now rituximab (RITUXAN®/MABTHERA®) (U.S. Pat. No. 5,736,137); the yttrium-[90]-labelled 2B8 murine antibody Y2B8 or ibritumomab tiuxetan (ZEVALIN®, Biogen Idec, Inc. U.S. Pat. No. 5,736,137); 2B8 deposited with ATCC under accession no. HB11388 on Jun. 22, 1993); murine IgG2a "B1," also called tositumomab, optionally labelled with $^{131}$I, to generate the "131I-B1" or "iodine I131 tositumomab" antibody (BEXXAR®) commercially available from Corixa (U.S. Pat. No. 5,595,721); murine monoclonal antibody "1F5" (e.g., Press et al (1987) Blood 69(2):584-591 and variants thereof including "framework patched" or humanized 1F5 (WO 2003/002607, Leung, S.; ATCC deposit HB-96450); murine 2H7 and chimeric 2H7 antibody (U.S. Pat. No. 5,677,180); ocrelizumab, a humanized variant of 2H7 and other 2H7 variants (WO 2004/056312; U.S. Pat. No. 5,721,108); HUMAX-CD20™ fully human, high-affinity antibody targeted at the CD20 molecule in the cell membrane of B-cells (Genmab, Denmark). See, for example, Glennie and van de Winkel, (2003) Drug Discovery Today 8:503-510 and Cragg et al (2003) Blood 101: 1045-1052; the human monoclonal antibodies set forth in WO 2004/035607 and WO 2005/103081 (Teeling et al., GenMab/Medarex); the antibodies having complex N-glycoside-linked sugar chains bound to the Fc region described in U.S. 2004/0093621 (Shitara et al.); monoclonal antibodies and antigen-binding fragments binding to CD20 (WO 2005/000901, Tedder et al.) such as HB20-3, HB20-4, HB20-25, and MB20-11; single-chain proteins binding to CD20 (U.S. 2005/0186216; U.S. 2005/0202534; U.S. 2005/0202028; U.S. 2005/0202023); CD20-binding molecules such as the AME series of antibodies, e.g., AME-133™ antibodies (WO 2004/103404; U.S. 2005/0025764); and CD20 antibodies with Fc mutations (WO 2005/070963); CD20-binding molecules (WO 2005/016969; U.S. 2005/0069545); bispecific antibodies (WO 2005/014618); humanized LL2 monoclonal antibodies (U.S. 2005/0106108); chimeric or humanized B-Ly1 antibodies to CD20 (WO2005/044859; U.S. 2005/0123546); =A20 antibody or variants thereof such as chimeric or humanized A20 antibody (cA20, hA20, respectively) and IMMUN-106 (U.S. 2003/0219433); and monoclonal antibodies L27, G28-2, 93-1B3, B-C1 or NU-B2 available from the International Leukocyte Typing Workshop (Valentine et al (1987) In: Leukocyte Typing III, McMichael, Ed., p. 440, Oxford University Press). Exemplary CD20 antibodies include chimeric, humanized, or human CD20 antibodies, such as rituximab, a humanized 2H7, chimeric or humanized A20 antibody such as HUMAX-CD20™, human CD20 antibody (Genmab), and immunoglobulins/proteins binding to CD20 (Trubion Pharm Inc.).

An "intact" antibody is one which comprises an antigen-binding variable region as well as a light chain constant domain (CL) and heavy chain constant domains, CH1, CH2 and CH3. The constant domains may be native sequence constant domains (e.g., human native sequence constant domains) or amino acid sequence variant thereof.

The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g., B cell receptor; BCR), etc.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

The term "amino acid sequence variant" refers to polypeptides having amino acid sequences that differ to some extent from a native sequence polypeptide. Ordinarily, amino acid sequence variants will possess at least about 70% sequence identity with at least one receptor binding domain of a native antibody or with at least one ligand binding domain of a native receptor, and preferably, they will be at least about 80%, more preferably, at least about 90% homologous by sequence with such receptor or ligand binding domains. The amino acid sequence variants possess substitutions, deletions, and/or insertions at certain positions within the amino acid sequence of the native amino acid sequence. Amino acids are designated by the conventional names, one-letter and three-letter codes.

"Sequence identity" is defined as the percentage of residues in the amino acid sequence variant that are identical after aligning the sequences and introducing gaps, if necessary, to achieve the maximum percent sequence identity. Methods and computer programs for the alignment are well known in the art. One such computer program is "Align 2," authored by Genentech, Inc., which was filed with user documentation in the United States Copyright Office, Washington, D.C. 20559, on Dec. 10, 1991.

Protein Expression and Production

Recombinant proteins are expressed by cloning DNA from vectors and methods known in the art. Proteins for the polyelectrolyte purification methods of the invention may be produced from suitable host cells such as prokaryote, yeast, and higher eukaryote cells. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for CD20 binding antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183, 070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibodies may be derived from multicellular eukaryotic organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Propagation of vertebrate cells in culture (tissue culture) has become a routine procedure. Examples of useful mammalian host cell lines are monkey kidney CV1 line transformed by SV40 (COS-7); human embryonic kidney line (293 or 293 cells subcloned for growth in suspension culture, Graham et al (1977) J. Gen Virol. 36:59) baby hamster kidney cells (BHK); Chinese hamster ovary cells/−DHFR(CHO, Urlaub et al (1980) Proc. Natl. Acad. Sci. U.S.A. 77:4216) Mather (1980) Biol. Reprod. 23:243-251; monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2, HB 8065); mouse mammary tumor (MMT 060562); TRI cells (Mather et al (1982) Annals N.Y. Acad. Sci. 383:44-68); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

The host cells used to produce antibodies for the methods of this invention may be cultured in a variety of media. Commercially available growth media such as Ham's F10 (Sigma), Minimal Essential Medium (MEM), (Sigma), RPMI-1640 (Sigma), and Dulbecco's Modified Eagle's Medium ((DMEM), Sigma) are suitable for culturing the host cells. In addition, any of the media described in Ham et al (1979) Meth. Enz. 58:44, Barnes et al (1980) Anal. Biochem. 102:255, U.S. Pat. Nos. 4,767,704; 4,657,866; 4,927,762; 4,560,655; 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as MES and HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Once a harvested cell culture fluid containing the protein of interest has been obtained, its separation from the other proteins produced by the cell is usually attempted using a combination of different chromatography techniques. These techniques separate mixtures of proteins on the basis of their charge, degree of hydrophobicity, or size. Several different chromatography resins are available for each of these techniques, allowing accurate tailoring of the purification scheme to the particular protein involved. The essence of each of these separation methods is that proteins can be caused either to move at different rates down a long column, achieving a physical separation that increases as they pass further down the column, or to adhere selectively to the separation medium, being then differentially eluted by different solvents. In some cases, the desired protein is separated from impurities when the impurities specifically adhere to the column, and the protein of interest does not, that is, the protein of interest is present in the "flow-through."

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration, such as antibodies which are secreted to the periplasmic space of E. coli (Carter et al (1992) Bio/Technology 10:163-167). The cell paste may be thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

Traditional methods of purifying proteins expressed from cells include hydroxylapatite chromatography, ion exchange chromatography, affinity chromatography, hydrophobic interaction chromatography, gel electrophoresis, dialysis, and combinations thereof (Fahrner, R. L. et al (2001) Biotechnol. Genet. Eng. Rev. 18:301-327). Protein A is commonly used as an affinity ligand which can immobilized on various supports and allows for initial stage enrichment of the harvested cell culture fluids (HCCF) containing expressed proteins. Protein A is a useful adsorbent for affinity chromatography of proteins, such as antibodies, which contain an Fc region. Protein A is a 41 kD cell wall protein from *Staphylococcus aureas* which binds with a high affinity (about $10^{-8}$ M to human IgG) to the Fc region of antibodies (Sulkowski, E. (1987) Protein Purification: Micro to Macro, pgs 177-195; Chadha et al. (1981) Preparative Biochemistry 11(4):467-482; Reifsnyder et al (1996) J. Chromatography 753:73-80; U.S. Pat. Nos. 6,127,526; 6,333,398). Protein A may be immobilized onto a solid phase such as glass, silica, agarose or polystyrene. The solid phase may be a purification column or a discontinuous phase of discrete particles such as a controlled pore glass column or a silicic acid column, or coated with a reagent (such as glycerol) which is intended to prevent nonspecific adherence of contaminants to the solid phase (U.S. Pat. No. 6,870,034). The PROSEP A™ column, commercially available from Bioprocessing Limited, is an example of a Protein A controlled pore glass column which is coated with glycerol. Other examples of columns contemplated herein include the POROS 50 A™ (polystyrene) column or rProtein A SEPHAROSE FAST FLOW™ (agarose) column. The solid phase for the Protein A chromatography may be equilibrated with a suitable buffer. For example, the equilibration buffer may be 25 mM Tris, 25 mM NaCl, 5 mM EDTA, pH 7.1.

When immobilized onto chromatography media, protein A provides a technique for purifying recombinant antibodies because it can selectively bind antibodies in complex solutions, allowing impurities such as host cell proteins and small molecules to flow through. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al (1983) J. Immunol. Meth. 62:1-13). Protein G is recommended for all mouse isotypes and for human γ3 (Guss et al (1986) EMBO J. 5:15671575). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Polyelectrolytes

Polyelectrolytes are water-soluble polymers comprised of charged monomer units. The monomer units of a polyelectrolyte of the invention bear an electrolyte (charged functionality) group which undergoes proton dissociation (ionization) in aqueous solutions according to acidity (pH). Exemplary charged functionality of polyelectrolytes include, but are not limited to, sulfonic acid, phosphonic acid, carboxylic acid, and amines, and their respective ions: sulfonate, phosphonate, carboxylate, and ammonium. The dissociation affects the solution's ionic strength and electrical conductivity.

Polyelectrolytes useful for the methods of the invention may have a molecular weight ranging from about a thousand (1000) daltons (Da) to about a million (1,000,000) daltons. The polyelectrolytes of the invention may be used as a mixture of a certain type of repeating monomeric unit but with a broad range of chain lengths, i.e. a range of molecular weight from about 1200 daltons (Da) to about a million (1,000,000) daltons. The mixture may be a narrow range, for example from about 1200 Da to about 2400 Da, or from about 4000 Da to about 8000 Da. The average molecular weight and the profile of the molecular weight distribution may be controlled under certain polymerization conditions of the monomeric units such as concentration, polymerization initiator or catalyst, temperature, or time. The average molecular weight and the profile of the molecular weight distribution of a polyelectrolyte may also be selected for under certain preparative purification methods.

Negatively charged, anionic polyelectrolytes and positively charged, cationic polyelectrolytes may be used in the precipitation reaction. When the solution pH is less than the pI of a particular antibody, the antibody is positively charged. Under these conditions, a cationic polyelectrolyte may precipitate impurities and leave the antibody of interest in solution. Conversely, an anionic polyelectrolyte may precipitate the antibody forming a protein-polyelectrolyte precipitate, leaving impurities in solution. Other factors in the selection of polyelectrolytes for the methods of the invention include functional group stability and reactivity, molecular weight, charge density and chain stiffness.

The polyelectrolytes of the invention include polyampholytes which bear both cationic and anionic charged functionality.

Exemplary polyanion polyelectrolytes of the invention include: polyacrylic acid (PAA), polyvinylsulfonate (PVS), polystyrenesulfonic acid (PSS), poly(4-vinylbenzenesulfonate metal salt)), polymethacrylate (PMA), polyacrylamidomethylpropanesulfonate (PAMPS), carboxymethylcellulose (CMC), maleic anhydride-styrene copolymer (MAS, maleic anhydride-vinylmethyl ether copolymer (MAVE), polyaspartate, polyglutamate, dextran sulfate, pectin, alginate, and glycosaminoglycans such as chondroitin sulfate, heparin/heparan sulfate, and hyaluronic acid; and all salts and copolymers thereof.

Polyacrylic acid (PAA) and polyvinylsulfonic acid (PVS), and their anions, polyacrylate and polyvinylsulfonate, respectively, are useful polyelectrolytes for the methods of the invention. PAA has similar structural properties to PVS. Both are polymeric and have linear carbon backbones. The two polyelectrolytes differ in their functional groups. PVS has a sulfonic acid functional group giving it a pKa of approximately one. By contrast PAA has a carboxylic acid function group and a pKa of approximately five. PVS is available in a single molecular weight determined to be an average of 1800 Da by size exclusion, where average n is about 10-20, with dynamic light scattering detection. PAA is commercially available in multiple molecular weights, including 1200 and 8000 where average n is about 15-20 and 100-120, respectively. PAA and PVS were purchased from Sigma-Aldrich Co., St. Louis Mo., Polysciences Inc., Warrington, Pa., and Carbomer, Inc., San Diego, Calif.

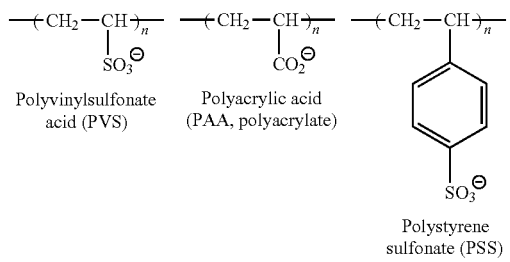

Polyvinylsulfonate acid (PVS)

Polyacrylic acid (PAA, polyacrylate)

Polystyrene sulfonate (PSS)

Exemplary positively charged, polycation polyelectrolytes of the invention include: polyarginine (PLA, including poly-L-arginine hydrochloride: Sigma-Aldrich P-4463, MW 5-15 kDa, P-7762 MW 15-70 kDa, P-3892, MW>70 kDa, CAS No. 26982-20-7, and poly-L-arginine sulfate, Sigma-Aldrich P-7637 MW 15-50 kDa, CAS No. 26700-68-5); polylysine (e.g. poly-L-lysine hydrochloride CAS Number: 26124-78-7, Sigma-Aldrich: P-2658 MW 15-30 kDa, CAS No. 26124-78-7, PLL, Jacobson, B. S. and Branton, D. (1977) Science 195, 302), polyornithine (e.g. poly-L-ornithine, Sigma-Aldrich P-2533 MW 15-30 kDa, CAS No. 26982-21-8), polyvinylguanidine (poly(vinylguanidine), U.S. Pat. No. 6,087,448), polydiallyldimethylammonium chloride, poly (N-ethyl-4-vinylpyridinium bromide), polymethylacrylamidopropyltrimethylammonium chloride, polyvinylbenzyltrimethylammonium chloride, and polyhistidine.

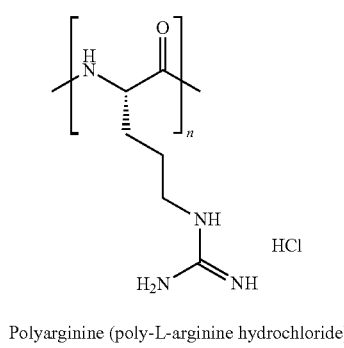

Polyarginine (poly-L-arginine hydrochloride)

-continued

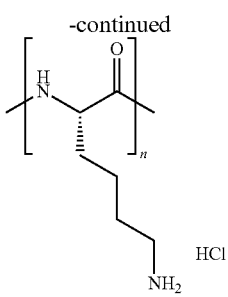

Polylysine (Poly-L-lysine hydrochloride)

Polyelectrolyte Precipitation in the Purification of Monoclonal Antibodies

Polyelectrolyte precipitation can be used to separate antibodies from impurities during purification. These impurities include host cell impurities such as CHO proteins (CHOP) and *E. coli* proteins (ECP), cell culture components such as insulin, gentamicin, and DNA, in-process impurities such as leached protein A, and product-related impurities such as antibody aggregates and fragments. The precipitation step may serve as a replacement to existing chromatography separations. Alternatively, polyelectrolyte precipitation of proteins may be used as a direct capture step from a harvested cell culture fluid (HCCF) from eukaryotic or prokaryotic culture, or as an intermediate purification step. Also, polyelectrolyte precipitation may be used as a clarification step in protein purification, clarifying cell culture fluid, including the HCCF. Polyelectrolytes may form a flocculent material in a cell culture fluid which settles and allows rapid and efficient clarification, enrichment, precipitation, or purification of mixtures containing a protein, such as an antibody expressed in prokaryotic or eukaryotic cell culture. Polyelectrolyte purification methods of the invention may supplant harvest operations such as centrifugation, filtration, and chromatography operations. The polyelectrolyte purification methods of the invention provide surprising and unexpected benefits in purifying proteins, such as antibodies.

The conditions to be optimized for polyelectrolyte precipitation include solution pH, conductivity, buffers, protein concentration, polyelectrolyte concentration, as well as rate and type of agitation, and the rate of polyelectrolyte addition.

The precipitation may be performed in a reactor with agitation. The pH and conductivity of the antibody pool may be adjusted to target conditions based on the optimal conditions identified from solubility curves. The polyelectrolyte is added and mixed. The rate and type of agitation may influence precipitation efficiency and time to precipitate. The precipitation follows the addition of the polyelectrolyte. The precipitant is separated from the supernatant using filtration or centrifugation. For anionic polyelectrolyte precipitation where filtration is used, the precipitant is washed through with wash buffer. The precipitant comprising an antibody would subsequently be re-suspended and processed downstream. It may also be possible to perform the precipitation in-line, i.e. without a mixing vessel, wherein the antibody pool would be adjusted to the target pH and the polyelectrolyte would then be added. Complete precipitation would not occur until the pool was diluted which could be performed in-line to either the filtration apparatus or the centrifuge. Alternatively, following adjustment of the antibody pool to the target pH, the dilution would be performed inline, followed by in-line addition of the polyelectrolyte prior to the filtration apparatus or centrifuge.

In one illustration, human growth hormone (pI 5.2) when crystallized or precipitated in a buffer at pH 7, would be negatively charged and therefore would interact or complex with cationic polyelectrolytes. Similarly, monoclonal antibodies, such as rituximab and trastuzumab, with pIs greater than 9, would be able to complex with anionic polyelectrolytes in neutral buffers. The estimation of a protein net charge can be calculated once the amino acid sequence is ascertained by publicly available programs. Acidic proteins, those proteins having a higher content of aspartic acid (pKa 4.5) and glutamic acid (pKa 4.5), typically have pIs lower than 6 to 6.4. On the other hand, basic proteins, those proteins having a higher content of histidine (pKa 6.2), lysine (pKa 10.4) and arginine (pKa 12), typically have pIs greater than about 7.5 to 8. In contrast to both, neutral proteins, those typically having similar amounts of acid and basic amino acid residues, have pIs that are neutral (pIs are typically about 6.5 to 7.4).

Although not a comprehensive list, some examples of pI for various therapeutic proteins are as follows: recombinant human erythropoietin (pI 4); dornase alfa, rhDNase (PULMOZYME™) (pI 5); etanercept (ENBREL™) (pI 5.1); insulin (pI 5.4); granulocyte colony stimulating factor (pI 5.5-5.9); TNF alpha (pI 5.6); fibrolase (pI 6.7); IL-1 beta (pI 6.9); recombinant tissue plasminogen activator (pI 6.5-8.5); Orthoclone OKT3 (PI 6.7-7.2); factor VIII (pI 7-7.6); bovine somatotropin (pI 7.4); Interleukin 2 (pI 7.44); Insulin-like growth factor-1 (pI 8.4) and Aprotinin (pI 10.5).

The anionic polyelectrolyte precipitation method was evaluated as the replacement for the cation exchange (SPSFF) step for several exemplary antibodies (anti-CD20 rhuMab 2H7, rhuMab DR5 Apomab, and anti-cMet), and also as a replacement for the protein A (Prosep vA) step for rhuMab 2H7 (ocrelizumab). Other antibodies, and other proteins, may be purified by the polyelectrolyte precipitation methods described herein. Solubility curves were used to identify the effective or optimum precipitation conditions (pH, conductivity and polymer concentration) for the three antibodies. A polyelectrolyte precipitation step demonstrated the ability to reduce host cell proteins, such as Chinese Hamster Ovary proteins (CHOP) and *E. coli* proteins (ECP), leached protein A, small molecules such as insulin and gentamicin as well as antibody fragments and aggregates. The polyelectrolyte precipitation step did not have a negative impact on the biological activity of 2H7 as measured by CDC activity. Polyelectrolyte PVS was removed from the precipitated protein to a level less than 1 µg/mL using anion exchange (QSFF) chromatography.

Figure 2:
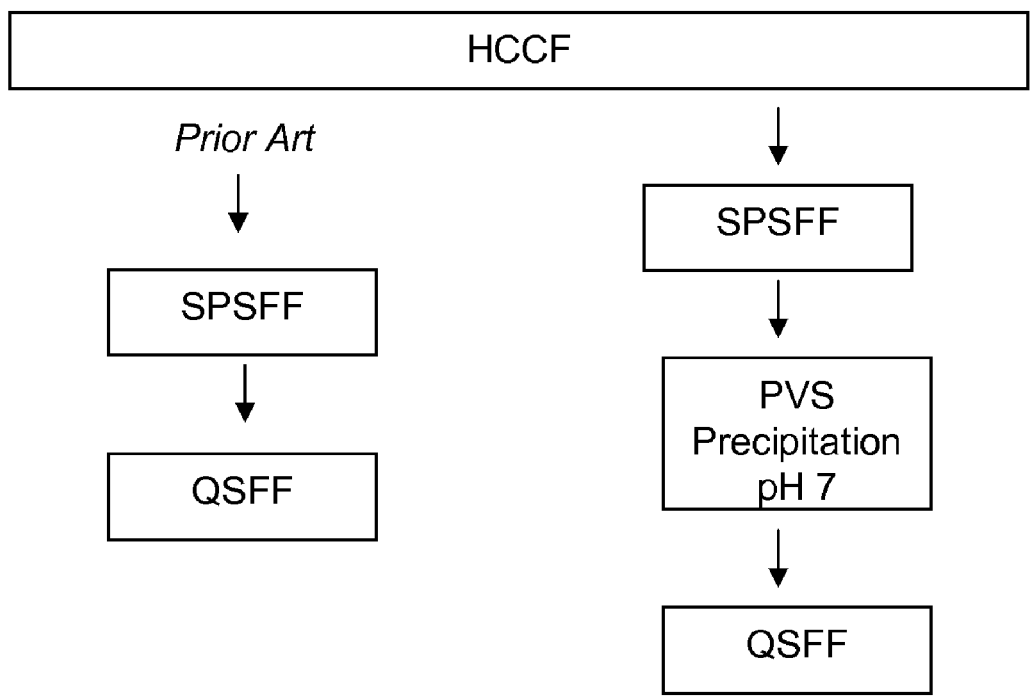
FIG. 2 shows process steps of purification of SPSFF pool purified from harvested cell culture fluid (HCCF) followed by: left column—QSFF; or right column—PVS precipitation at pH 7 then QSFF.
Figure 3:
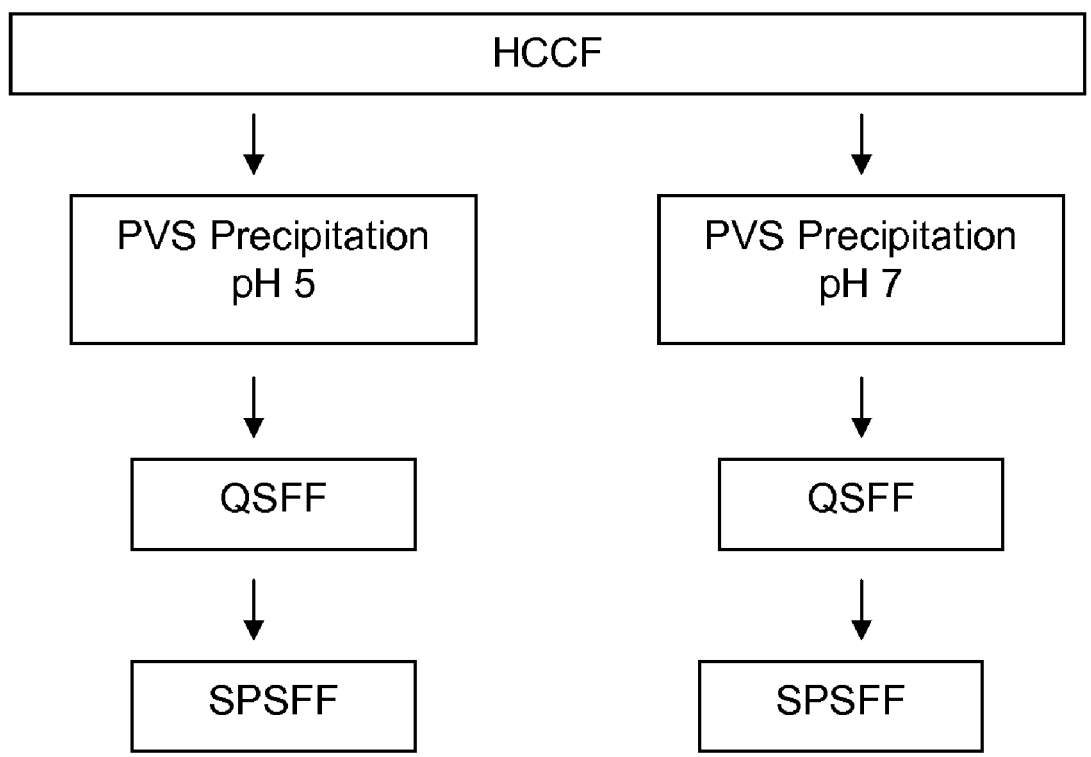
FIG. 3 shows process steps for the direct capture and purification of the antibody from HCCF: left column—PVS precipitation at pH 5, followed by QSFF then SPSFF; right column—PVS precipitation at pH 7, followed by QSFF then SPSFF.

The various series of process steps are illustrated in the flow diagrams of FIGS. 1-3. The steps were combined and omitted to judge their results on protein purification and process efficiency. One standard process currently practiced in the art for expressed protein purification from harvested cell culture fluid (HCCF) uses three chromatography steps: (1) a protein A capture (Prosep vA), (2) cation exchange (SPSFF) and (3) anion exchange (QSFF), shown as the left column in FIG. 1. Purification was attempted by protein A capture followed directly by anion exchange (middle column, FIG. 1). The cation exchange step may be replaced with a PVS precipitation step at pH 7 (right column, FIG. 1). The harvested cell culture fluid may be processed without protein A capture by an initial cation exchange followed directly by anion exchange (left column, FIG. 2), or by PVS precipitation at pH 7 followed by anion exchange (right column, FIG. 2). Polyelectrolyte precipitation may be conducted as a direct capture from HCCF, followed by anion exchange then cation exchange chromatography (FIG. 3). The polyelectrolyte precipitation was conducted at pH 5 (left column, FIG. 3) and at pH 7 (right column, FIG. 3).

Selection of Precipitation Conditions for an Anti-CD20 Antibody, rhuMab 2H7

Figure 6:
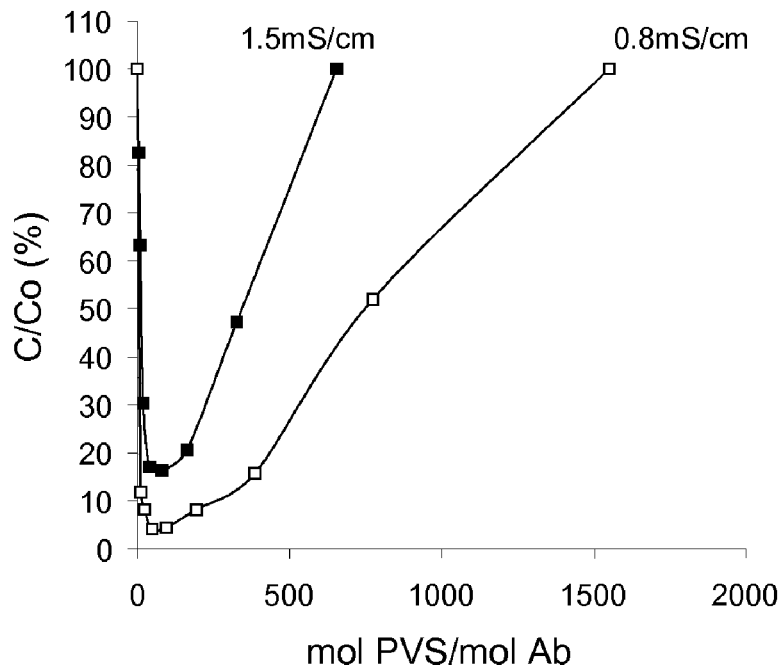
FIG. 6 shows rhuMab 2H7 solubility curves in PVS (1800 Da) at pH 7 at 0.8; and 1.5 mS/cm (SPSFF capture pool)
Figure 7:
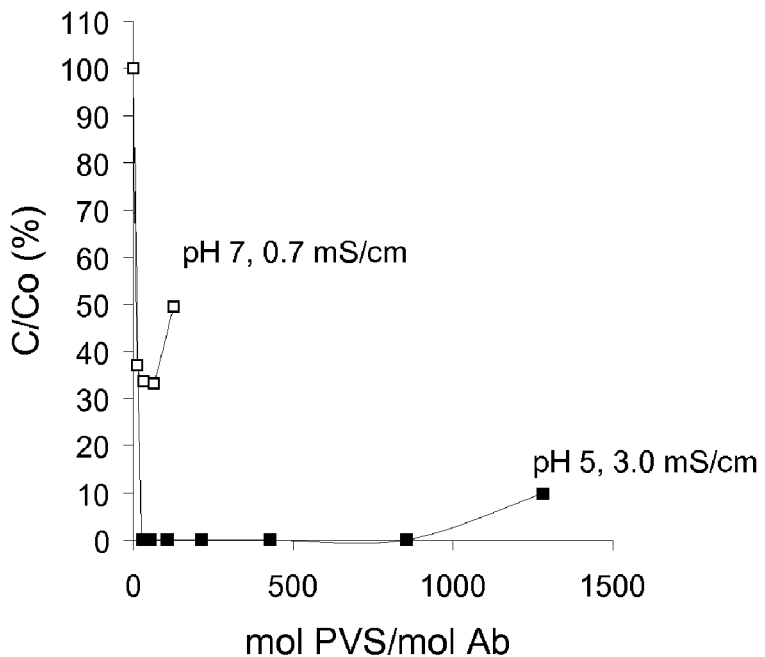
FIG. 7 shows rhuMab 2H7 solubility curves in PVS (1800 Da) at pH 5 and 3.0 mS/cm; and at pH 7 and 0.7 mS/cm (HCCF).

Solubility curves were generated for the recombinant humanized anti-CD20 monoclonal antibody, rhuMab 2H7, over a range of ionic strengths. Solubility curves are a plot of residual protein left in the supernatant following precipitation (expressed as a percentage) versus concentration of PVS expressed as moles of PVS/moles of antibody. Solubility curves were generated for protein A pool at pH 5 and pH 7 (FIGS. 4 and 5), the SPSFF pool (FIG. 6) when used as a direct capture step at pH 7 and for HCCF at pH 5 and pH 7 (FIG. 7). These curves were used to select the pH, ionic strength and PVS concentration at which the preparative scale precipitations would be performed.

Figure 4:
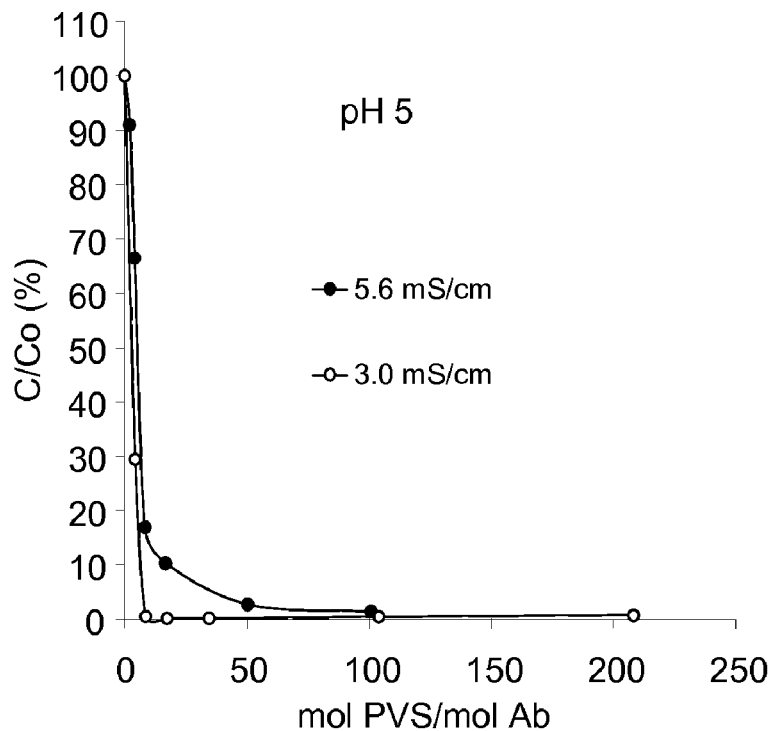
FIG. 4 shows rhuMab 2H7 solubility curves in PVS (1800 Da) at pH 5 at 3.0 and 5.6 mS/cm (protein A pool). mS=millisiemens, a unit of conductivity
Figure 5:
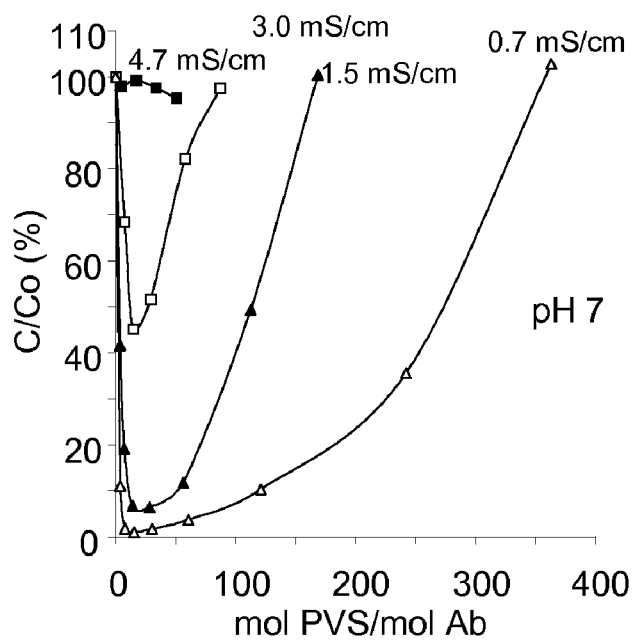
FIG. 5 shows rhuMab 2H7 solubility curves in PVS (1800 Da) at pH 7 at 0.7, 1.5, 3.0 and 4.7 mS/cm (protein A pool)

Precipitation of Protein A Pool (FIG. 4 and FIG. 5)

With increasing PVS concentration, there was immediate precipitation at pH 5, as indicated by a decrease in the percent antibody remaining in solution—$C/C_o$, i.e. the concentration of antibody in solution divided by the total antibody (FIG. 4). C/Co (%) is the percent (%) protein not precipitated divided by the initial protein. When C/Co (%) is 0%, then there was complete precipitation.

By decreasing ionic strength, it was possible to achieve a greater level of precipitation (4.7 mS/cm versus 3.0 mS/cm where mS is millisiemens, a unit of conductivity). At pH 7, a dilution was required to achieve significant precipitation (FIG. 5). With decreasing conductivity, there was an increase in precipitation. Complete precipitation was observed at a conductivity of 0.7 mS/cm. At a particular conductivity, once a maximum level of precipitation was observed, the addition of additional PVS caused the precipitant to redissolve.

Precipitation of SPSFF pool (FIG. 6) and HCCF (FIG. 7): Similar trends were observed with the SPSFF pool and HCCF. With decreasing conductivity, there was an increase in precipitation. At a particular conductivity, once a maximum level of precipitation was observed, the addition of additional PVS caused the precipitant to re-dissolve.

Assessing the Impact of Polyelectrolyte Molecular Weight

Figure 8:
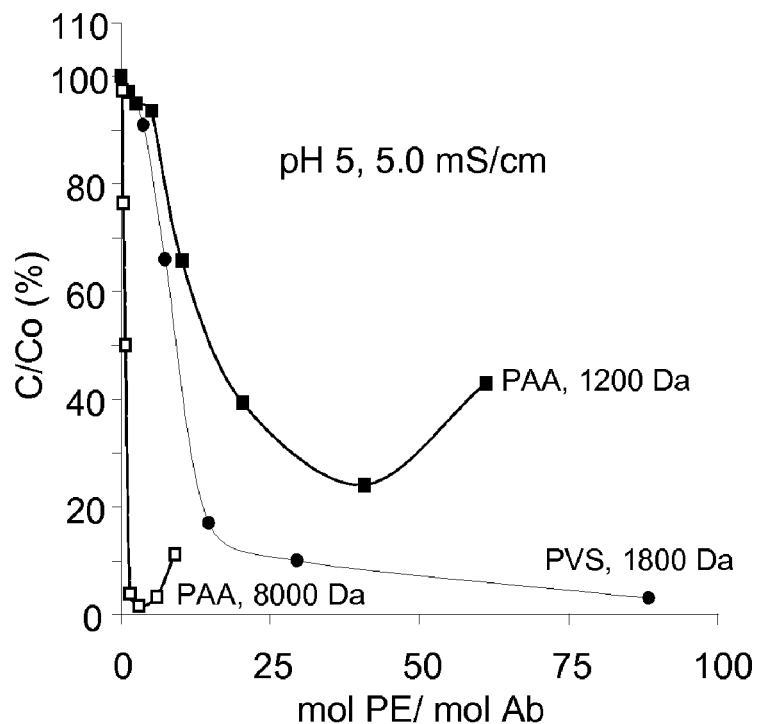
FIG. 8 shows solubility curves comparing PVS (1800 Da) precipitation to PAA (1200 and 8000 Da) precipitation at pH 5, 5 mS/cm of the anti-CD20 antibody, 2H7.
Figure 9:
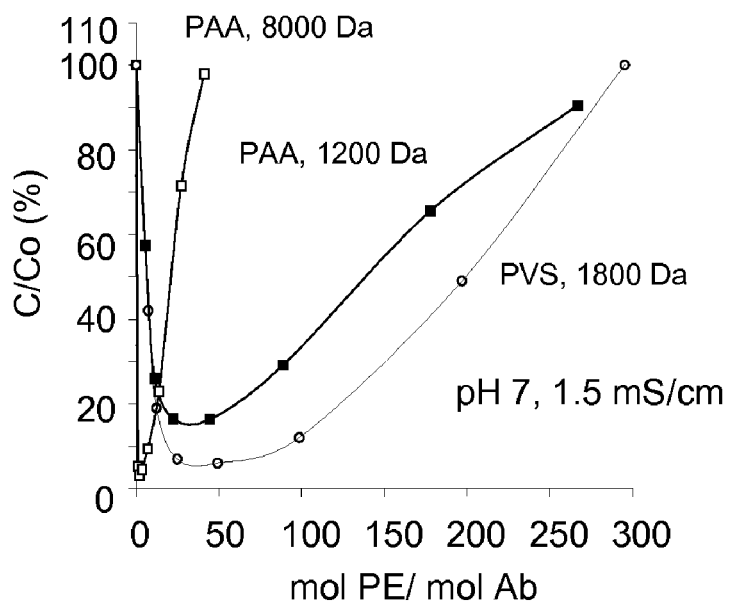
FIG. 9 shows solubility curves comparing PVS (1800 Da) precipitation to PAA (1200 and 8000 Da) precipitation at pH 7, 1.5 mS/cm of the anti-CD20 antibody, 2H7.

Solubility curves were also generated comparing PVS to PAA. Solubility curves are a plot of residual protein left in the supernatant following precipitation (expressed as a percentage) versus concentration of polyelectrolyte expressed as moles of polyelectrolyte/moles of antibody. Solubility curves for PAA (1200 & 8000 Da) and PVS (1800 Da) over a range of equivalents of polyelectrolyte per anti-CD20 antibody (rhuMab-2H7, pI 9.0, 150 kDa), measured at pH 5 (FIG. 8) and pH 7 (FIG. 9). The higher molecular weight form (8000 Da) of PAA, led to greater precipitation at pH 5 and a conductivity value of 5 mS/cm (FIG. 8) as compared to the lower molecular weight from (1200 Da) of PAA and (1800 Da) PVS polyelectrolytes (FIG. 8). A similar trend was observed at pH 7, 1.5 mS/cm (FIG. 9). The higher molecular weight 8000 Da PAA, led to greater precipitation at pH 7 and a conductivity value of 1.5 mS/cm as compared to the lower molecular weight 1200 Da PAA and 1800 Da PVS polyelectrolytes. The basic unit of conductance is the siemen (S), formerly called the mho. Conductivity measurements are temperature dependent. Conductivity values are expressed as mS/cm. In both cases, the larger PAA polyelectrolyte had a narrower operating range in terms of concentration of polyelectrolyte required to achieve maximum precipitation before further addition of polyelectrolyte caused the precipitant to re-dissolve. Increasing the polyelectrolyte molecular weight may allow the precipitation to be performed at higher conductivities.

Figure 10:
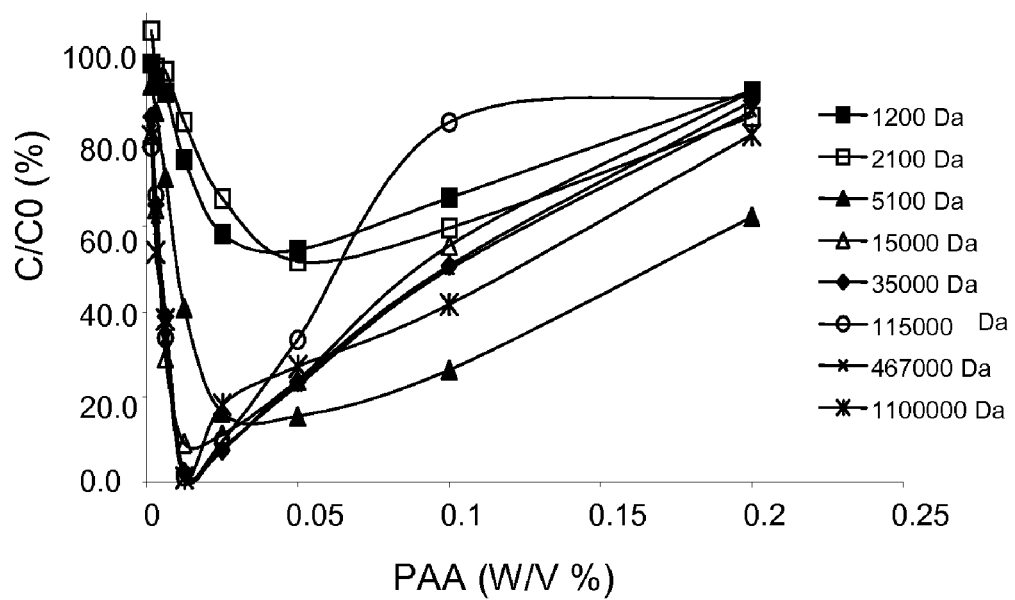
FIG. 10 shows anti-CD20 antibody (rituximab) solubility curves at pH 7, 1.5 mS/cm comparing PAA with molecular weights ranging from 1200 to 1,100,000 Da.

The effect of polyelectrolyte molecular weight on an anti-CD20 antibody (rituximab) precipitation at pH 7 and 1.5 mS/cm was investigated with PAA within the molecular weight range of 1200 Da to 1,100,000 Da (FIG. 10). Increasing molecular weight resulted in increased precipitation under these conditions. At pH 7 and 1.5 mS/cm complete precipitation was not achieved until PAA with a molecular weight greater than 35,000 Da (35 kDa) was used.

Figure 33:
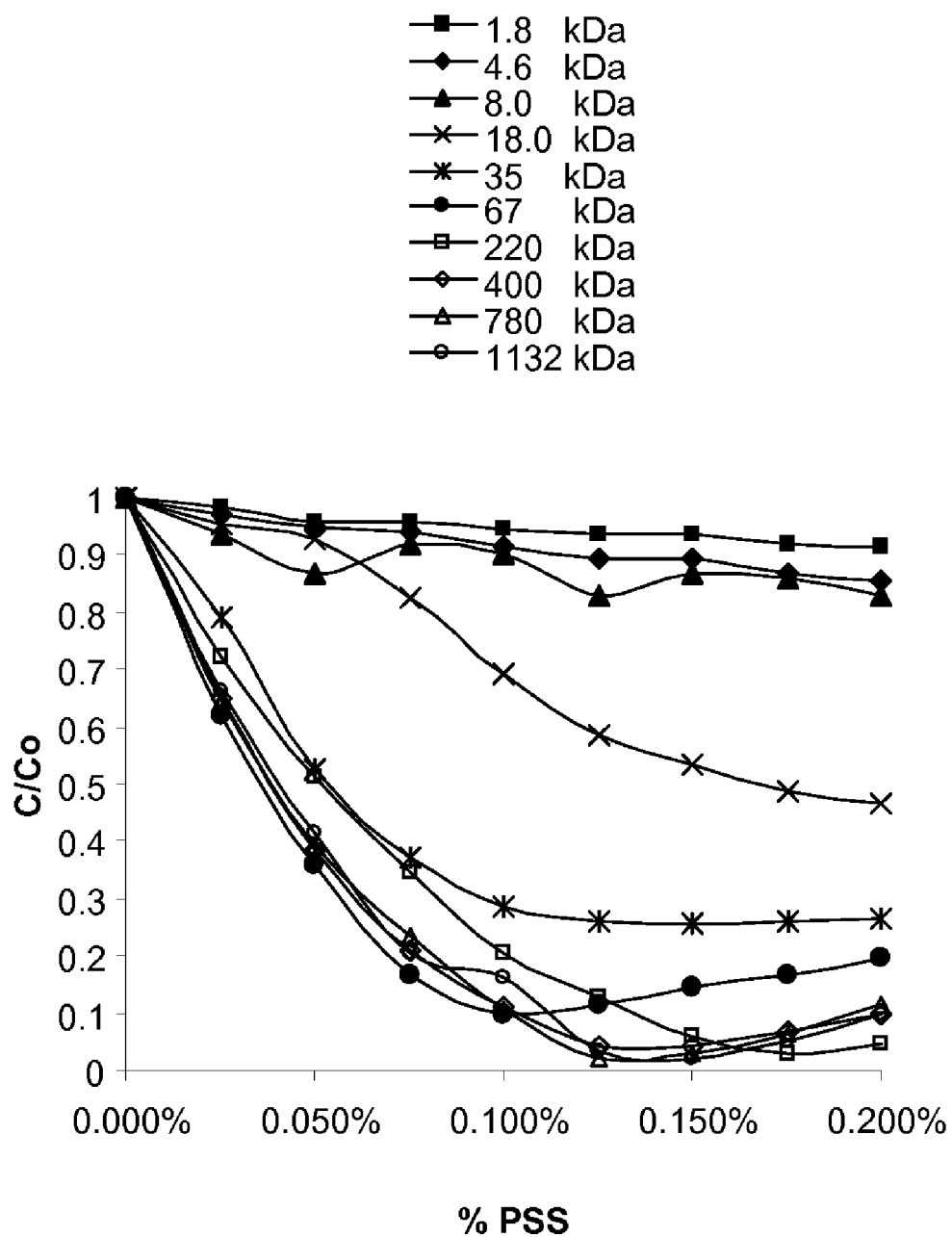
FIG. 33 shows humanized anti-CD20 solubility curves with 1800 Da to 1132 kDa samples of 0.00% to 0.20% polystyrene sulfonate (PSS) at pH 7 and 12 mS/cm conductivity.

The effect of polyelectrolyte molecular weight on the precipitation of a humanized anti-CD20 antibody at pH 7 and 12 mS/cm was also investigated with polystyrene sulfonate (PSS) within the molecular weight range of 1800 Da to 1,132,000 Da (FIG. 33). Solubility curves were generated for PSS precipitation of the humanized anti-CD20 antibody over this molecular weight range. Increasing molecular weight resulted in increased precipitation under these conditions. At pH 7 and 12 mS/cm complete precipitation was not achieved until PSS with a molecular weight greater than 220,000 Da (220 kDa) was used. Using PSS allows the precipitation to be performed at a higher conductivity and minimizes the need to lower the conductivity/ionic strength of pools to achieve complete precipitation The effect of polyelectrolyte molecular weight on impurity clearance was measured under the conditions of Table 1 and the downstream processing results are shown in Table 2. After the precipitation step, the PAA 8000 Da had higher levels of Chinese Hamster Ovary Proteins (CHOP) than the PAA 1200 Da or PVS (Table 2). At the QSFF pools, similar CHOP levels were observed for all pools independent of the molecular weight of the polyelectrolyte used in the purification. Both molecular weights of PAA reduced leached protein A and antibody fragments to similar levels and did not have a negative impact on aggregate levels.

DNA and reduce antibody aggregates, if present (FIG. 11). Insulin is removed by the previous protein A step. The PVS precipitation step reduced CHOP to similar levels as the SPSFF step. It also reduced leached protein A and antibody fragments. There was a reduction in gentamicin across the precipitation step, although not to the same extent as the SPSFF step. The DNA assay does not function in the presence of PVS so PVS clearance across the precipitation step could not be assessed. The addition of the precipitation step did not increase antibody aggregates or impact biological activity as measured by CDC activity (FIG. 11 and Table 3).

In order to provide a more challenging feedstock, HCCF was processed directly across a SPSFF column. The SPSFF pool had a 4 fold higher CHOP than the protein A pool when used as the initial capture step (FIG. 11). The % fragment was also higher than the protein A capture process (9.24% versus 0.24%). It is likely that a protease co-purified with the antibody across the cation exchange step resulting in clipping of the antibody. The PVS precipitation step reduced fragment by 5.63%. CHOP was reduced to 4.1 ng/mg through the process, compared to 71 ng/mg without a precipitation step. Gentamicin was also significantly reduced by the precipitation step (from 146 to 8 ng/mg). Insulin and DNA were reduced to low levels by the initial SPSFF capture step, so their clearance could not be assessed. The high fragment level in control run (SPSFF-QSFF) resulted in reduced CDC activity of 87% (Table 3). By contrast, the PVS precipitated run had 100% CDC activity.

TABLE 1

PAA precipitation conditions

| PAA MW | Pool pH | Pool conductivity | PAA (%) | PAA (mol) | 2H7 Antibody (mg/ml) | 2H7 Antibody (mol) | mol PVS/mol 2H7 |
|---|---|---|---|---|---|---|---|
| 1200 | 5 | 3.05 | 0.1 | 8.88E−05 | 3.46 | 2.53E−06 | 35 |
| 1200 | 7 | 0.78 | 0.0125 | 5.82E−05 | 0.66 | 2.52E−06 | 23 |
| 8000 | 5 | 4.99 | 0.1 | 7.38E−06 | 5.94 | 2/40E−06 | 3 |
| 8000 | 7 | 1.53 | 0.0125 | 3.83E−06 | 1.31 | 2.20E−06 | 2 |

TABLE 2

Summary of downstream processing results

| Polyelectrolyte | pH (−) | Step (−) | Yield (%) | CHOP (ng/mg) | Protein A (ng/mg) | Aggregate (%) | Monomer (%) | Fragment (%) |
|---|---|---|---|---|---|---|---|---|
| | | ProA | N/A | 1098 | 5 | 0.63 | 99.14 | 0.24 |
| | | Q | 100 | 25 (16) | 3 | 0.64 | 99.13 | 0.23 |
| PAA MW 1200 (Da) | pH 5 | ProA | N/A | 1098 | 5 | 0.63 | 99.14 | 0.24 |
| | | PAA | 82 | 117 | <2 | 0.69 | 99.22 | 0.09 |
| | | Q | 100 | 2.0 | <2 | 0.55 | 99.38 | 0.07 |
| | pH 7 | ProA | N/A | 1098 | 5.0 | 0.63 | 99.14 | 0.24 |
| | | PAA | 80 | 163 | <2 | 0.73 | 99.18 | 0.09 |
| | | Q | 99 | 1.7 | <2 | 0.64 | 99.25 | 0.10 |
| PAA MW 8000 Da | pH 5 | ProA | N/A | 1098 | 5 | 0.63 | 99.14 | 0.24 |
| | | PAA | 90 | 302 | <2 | 0.80 | 99.05 | 0.15 |
| | | Q | 103 | 2.6 | <2 | 0.58 | 99.33 | 0.09 |
| | pH7 | ProA | N/A | 1098 | 5 | 0.63 | 99.14 | 0.24 |
| | | PAA | 90 | 390 | <2 | 0.81 | 99.08 | 0.11 |
| | | Q | 100 | 2.3 | <2 | 0.65 | 99.25 | 0.10 |
| PVS MW 1800 Da | pH 7 | ProA | N/A | 1105 | 23 | 0.80 | 98.92 | 0.27 |
| | | PVS | 100 | 244 | 4.0 | 0.74 | 99.21 | 0.04 |
| | | Q | 92 | 1.1 | 2 | 0.68 | 99.29 | 0.03 |

Anti-CD20 Antibody Purification

Polyelectrolyte precipitation was initially evaluated as a replacement for the cation exchange chromatography step. The primary function of the cation exchange step is to reduce host cell impurities, remove leached protein, gentamicin, A PVS step was also evaluated as a direct capture step from HCCF. The PVS precipitation step at pH 7 removed insulin (FIG. 11). By contrast, the PVS precipitation step at pH 5 only partially reduced insulin levels. PVS precipitation at pH 7 removed 3-fold more host cell proteins than the precipitation at pH 5. The replacement of the final SPSFF step with an orthogonal chromatography method such as a hydrophobic interaction step may further reduce host cell impurities. With the pH 5 capture, there was a 4.66% increase in antibody fragments across the cation exchange step. This did not occur with the pH 7 capture step. This may suggest that at pH 5 (much like with the SPSFF capture step), an acidic protease was co-purified causing an increase in antibody fragments. The addition of the precipitation step did not impact biological activity as measured by CDC activity (Table 3). The Q Pools were analyzed for biological activity/potency using a complement dependent cytotoxicity (CDC) assay. This assay is based on measuring the ability of rhuMAb 2H7 to lyse WIL2-S cells in the presence of human complement.

TABLE 3

The effect of PVS precipitation on CDC activity

| Sample | Specific Activity (%) | Standard Deviation (%) |
|---|---|---|
| Controls: | | |
| HCCF-Protein A-SPSFF-QSFF | 99 | 2 |
| HCCF-Protein A-QSFF | 102 | 2 |
| HCCF-SPSFF-QSFF | 87 | 10 |
| PVS Precipitation: | | |
| HCCF-Protein A-PVS7-QSFF | 101 | 5 |
| HCCF-SPSFF-PVS7-QSFF | 100 | 5 |
| HCCF-PVS5-QSFF-SPSFF | 96 | 5 |
| HCCF-PVS7-QSFF-SPSFF | 95 | 0 |

Polyelectrolyte clearance (removal of polyelectrolyte from the re-suspended antibody) was determined using a FRET (fluorescence resonance energy transfer) assay based on the inhibition of RNAse A. PVS is a potent inhibitor of RNase A. The assay uses an RNA analog with a fluorescent label on one end and a quencher on the other. Once the RNA analog is cleaved by RNase A, the fluorescent label is released from the quencher yielding emission. The presence of PVS will inhibit the RNase A activity, limiting fluorescent emission. The amount of PVS can then be determined by comparing the observed fluorescence from a test sample to a standard curve. In all cases, PVS was cleared to less than 1 μg/μl on QSFF chromatography (Table 4).

TABLE 4

Quantifying PVS clearance after precipitation of antiCD20 antibody (2H7)

| Sample | Fluorescence (RFU) | PVS (mg/ml) |
|---|---|---|
| Control Q Pool (ProA-SP-Q) | 279 | <1 |
| Q loads with PVS (Average) | 40 | 606 |
| Q Pools | | |
| ProA-PVS-Q | 281 | <1 |
| HCCF-PVS 5-Q | 290 | <1 |
| HCCF-PVS 7-Q | 283 | <1 | rhuMab DR5 Apomab Purification

Figure 12:
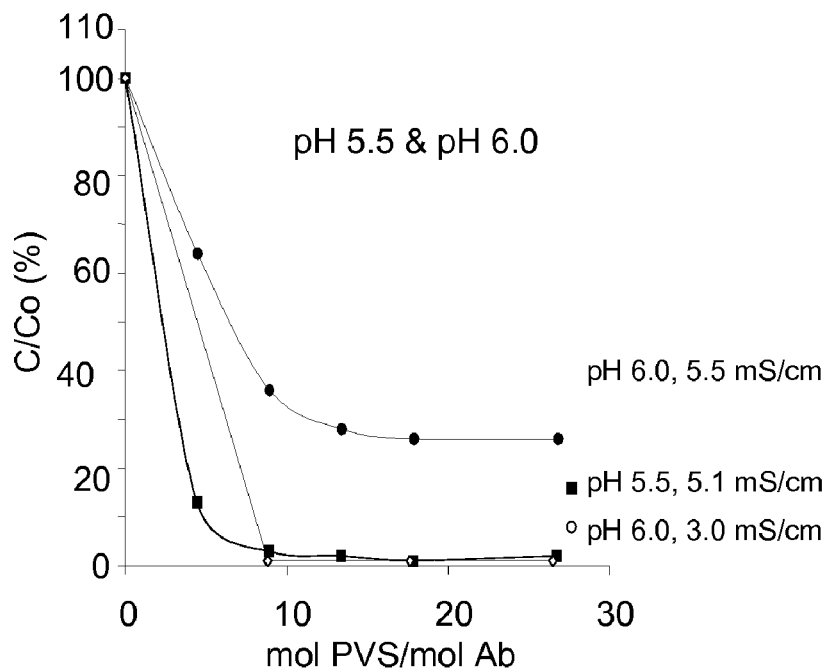
FIG. 12 shows Apomab solubility curves in PVS (1800 Da) at pH 5.5 and 5.1 mS/cm; pH 6.0 and 3.0 mS/cm; pH 6.0 and 5.5 mS/cm.
Figure 13:
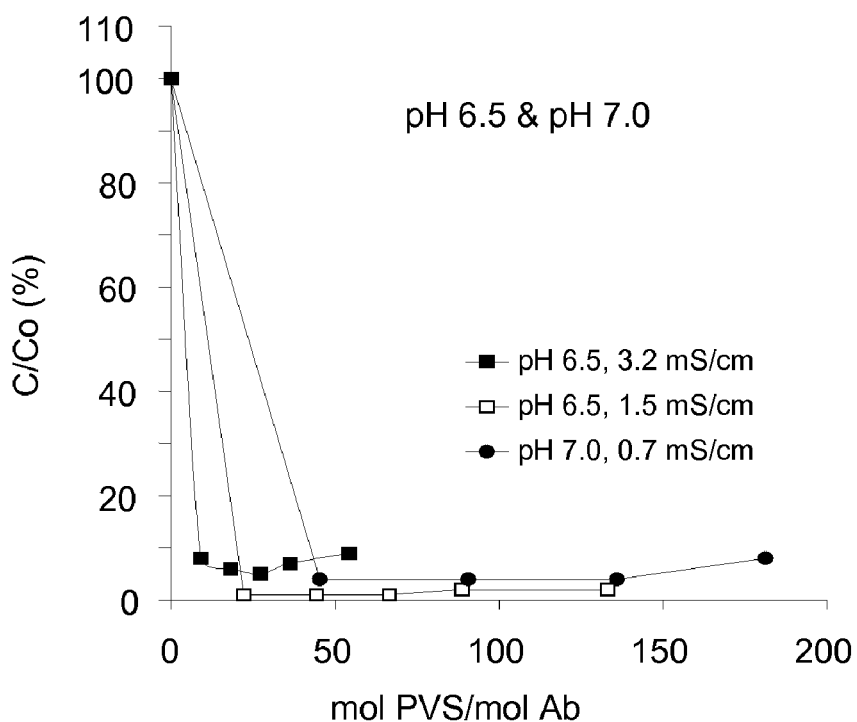
FIG. 13 shows Apomab solubility curves in PVS (1800 Da) at pH 6.5 and 1.5 mS/cm; pH 6.5 and 3.2 mS/cm; and pH 7.0 and 0.7 mS/cm.

A polyelectrolyte precipitation process was developed and applied to purification of the antibody rhuMAb DR5 Apomab (pI 8.0, 150 kDa). The Death Domain Containing Receptor-5 (DR5) proteins are members of the tumor necrosis factor (TNF) receptor family (U.S. Pat. Nos. 6,872,568; 6,743,625). The standard chromatography process uses Prosep vA, SPSFF and QSFF resins. The polyelectrolyte precipitation process was modified to remove a problematic host cell protein impurity, glutathione-s-transferase (GST). The Prosep vA step has a 0.5M TMAC wash, pH 5 as opposed to 0.4M potassium phosphate pH 7 wash. The SPSFF step is eluted in a shallow gradient giving a pool volume of approximately 12 column volumes. PVS precipitation was evaluated as a replacement for the SPSFF step. Solubility curves were generated over a pH range of 5.5 to 7.0. With increasing pH, a dilution to reduce ionic strength was required to achieve complete precipitation (FIGS. 12 and 13). In FIG. 12, a dilution to reduce ionic strength with increasing pH was required to achieve complete precipitation. At pH 5.5 and a conductivity of 5.1 mS/cm complete precipitation was observed. However, at pH 6 it was necessary to dilute the pool to 3 mS/cm to achieve complete precipitation. In FIG. 13, a dilution to reduce ionic strength with increasing pH was required to achieve complete precipitation. At pH 6.5, complete precipitation was observed at 1.5 mS/cm. At pH 7, it was necessary to dilute the pool to 0.7 mS/cm to achieve complete precipitation.

Figure 14:
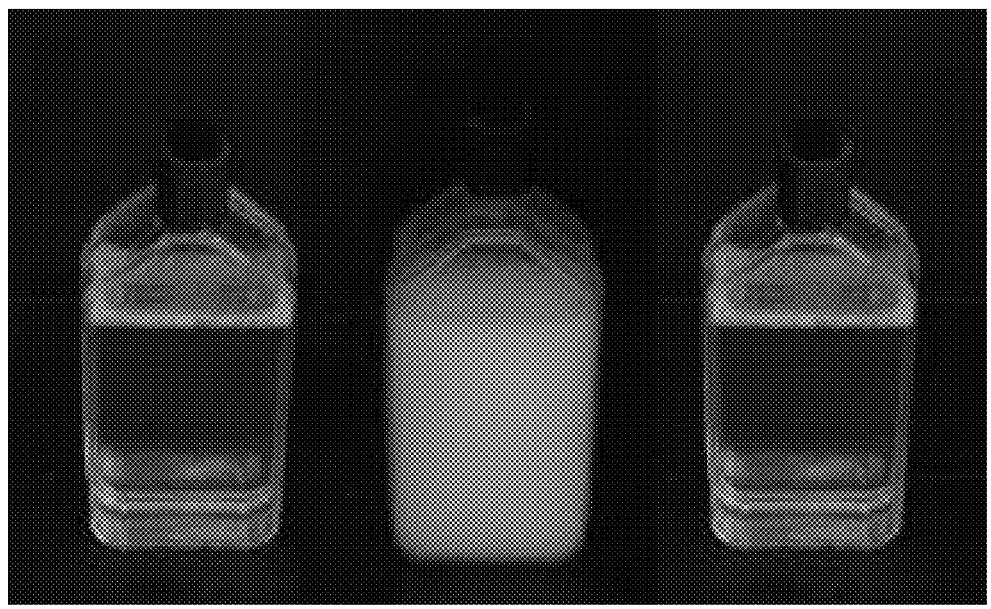
FIG. 14 shows a photograph of flasks containing Protein A pools of Apomab at pH 5.5 containing: (left) no PVS (0%), (center) 0.1% PVS (w/v), and (right) 1% PVS (w/v).

Once complete precipitation was achieved, the addition of additional PVS caused the precipitant to re-dissolve. This effect is illustrated by the photographs in FIG. 14. FIG. 14 illustrates the precipitation effect of 0.1% PVS (w/v) in a flask of Apomab in solution, and redissolution at 1% PVS (w/v). The solubility curves were used to select the precipitation conditions outlined in Table 5. PVS precipitation was performed between pH 5.5 and pH 7.0. With increasing pH, there was a slight decrease in yield but an improvement in CHOP and leached protein A clearance (Table 6). These pools were subsequently processed across a QSFF column and compared to the control runs (Table 6). An SPSFF step or PVS precipitation step was required to clear CHOP to <0.79 ng/mg and to clear leached protein A to <2 ng/mg. versus 17 ng/mg CHOP and 4 ng/mg leached protein A in the control run without an SPSFF or precipitation step. PVS precipitation also demonstrated the ability to reduce GST but not to the same level as the SPSFF step.

TABLE 5

Apomab precipitation conditions

| Pool pH (−) | Pool Conductivity (mS/cm) | PVS (%) | mol PVS/mol Ab |
|---|---|---|---|
| 5.5 | 5.1 | 0.100 | 18 |
| 6.0 | 3.0 | 0.100 | 35 |
| 6.5 | 1.5 | 0.100 | 70 |
| 7.0 | 0.8 | 0.100 | 177 |

TABLE 6

ApoMab purification - Downstream processing results for Apomab intermediate pools (a) and QSFF pools (b)

| (a) Intermediate Pools | Pro A Pool | SP Pool | PVS Precipitated Pool* | | | |
|---|---|---|---|---|---|---|
| | | | pH 5.5 | pH 6.0 | pH 6.5 | pH 7.0 |
| Yield (%) | N/A | 89 | 95 | 94 | 92 | 91 |
| CHOP (ng/mg) | 507 | 24 | 223 | 212 | 173 | 121 |
| GST (ng/mg) | 121 | <180 | <78 | <79 | <80 | <81 |
| Leached Protein (ng/mg) | 8 | <2 | 3 | 2 | 2 | <2 |

| (b) Q Pools | Pro A Pool | Controls | | Pro A-PVS-Q | | | |
|---|---|---|---|---|---|---|---|
| | | (PA-Q) | PA-SP-Q | pH 5.5 | pH 6.0 | pH 6.5 | pH 7.0 |
| Yield (%) | N/A | 100 | 94 | 99 | 101 | 101 | 99 |
| CHOP (ng/mg) | 507 | 17 (3) | <0.30 | <0.74 | <0.75 | <0.77 | <0.79 |
| GST (ng/mg) | 121 | 126 | 4 | 69 | 68 | 82 | 80 |
| Leached Protein (ng/mg) | 8 | 4 | <2 | <2 | <2 | <2 | <2 |

Anti-cMet Purification

Figure 15:
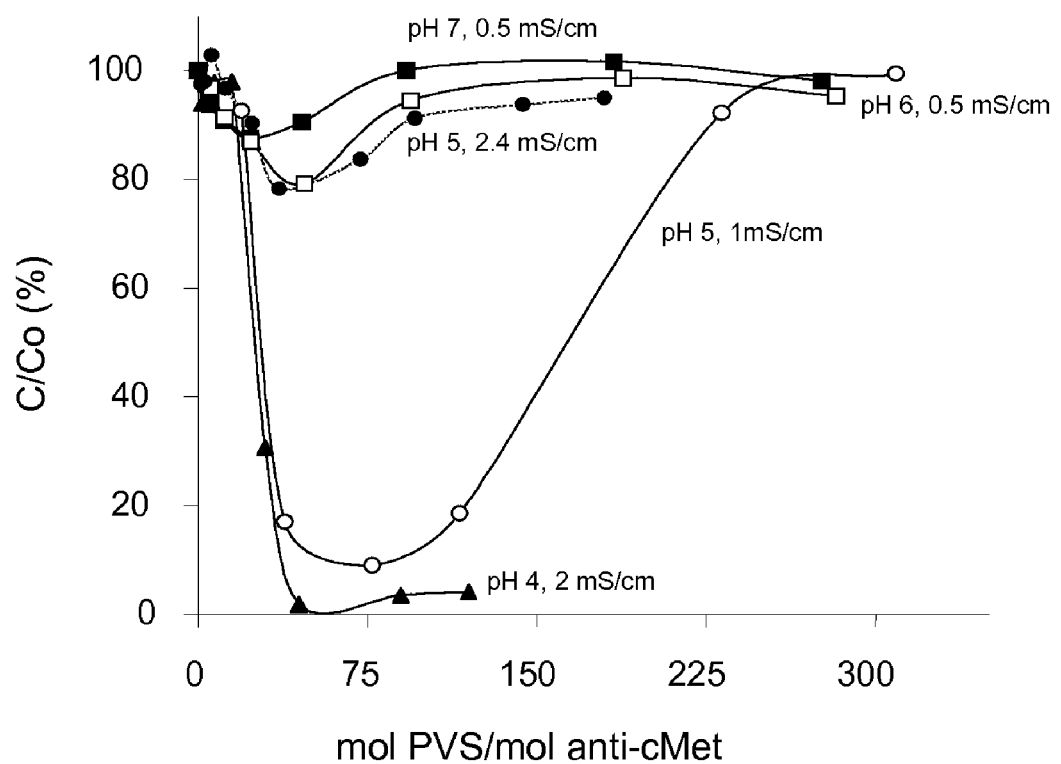
FIG. 15 shows anti-cMet solubility curves in PVS (1800 Da) at pH 4 and 2 mS/cm; pH 5 and 1 mS/cm; pH 5 and 2.4 mS/cm; pH 6 and 0.5 mS/cm; pH 7 and 0.5 mS/cm.
Figure 16:
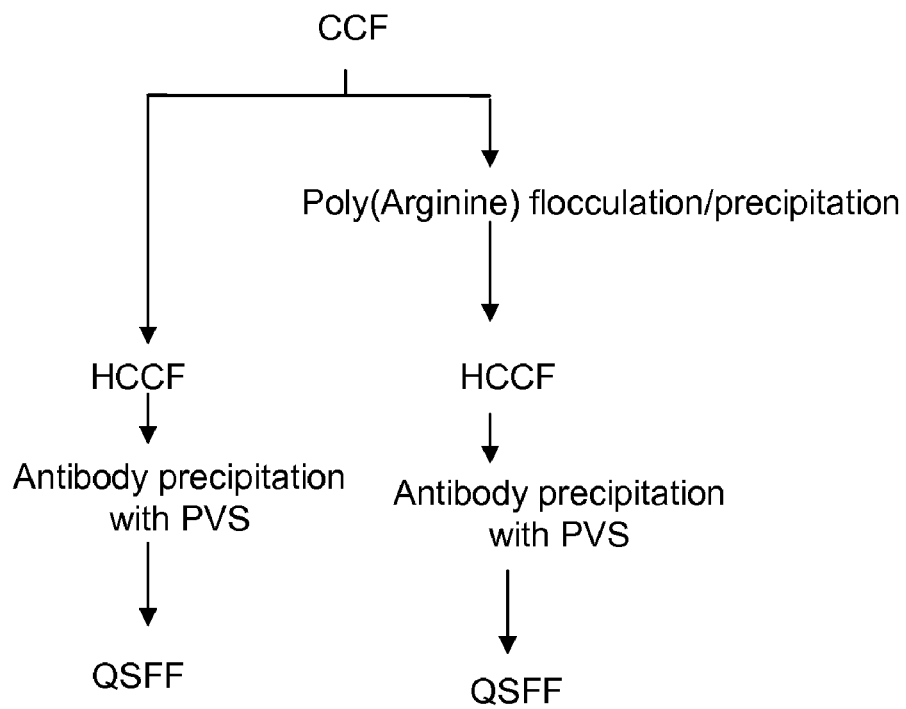
FIG. 16 shows process steps for the direct capture and purification of the rhuMab 2H7 antibody from CCF: left column—centrifugation to HCCF, followed by antibody precipitation with PVS, then QSFF; right column—polyarginine flocculation/precipitation of impurities, centrifugation to HCCF, antibody precipitation with PVS, then QSFF.
Figure 17:
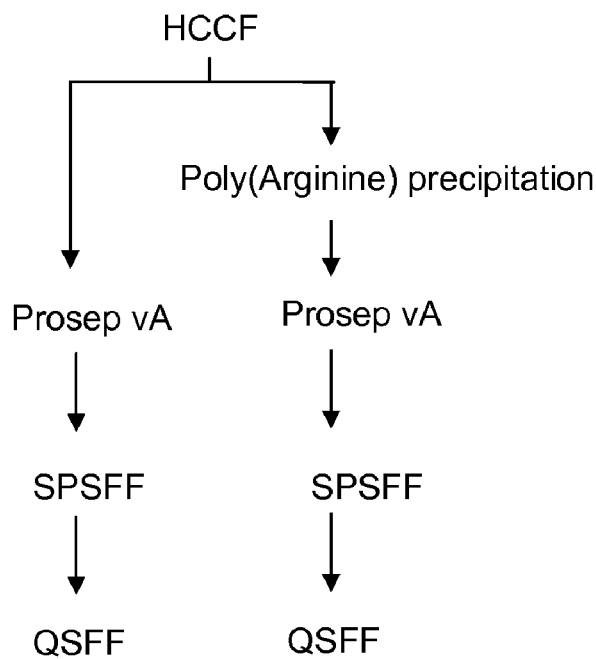
FIG. 17 shows process steps for the purification of the rhuMab 2H7 antibody from harvested cell culture fluid (HCCF) followed by: left column—Prosep vA, cation exchange chromatography (SEPHAROSE™ fast flow, SPSFF) then anion exchange chromatography (QSFF); right column—polyarginine precipitation, Prosep vA, SPSFF, then QSFF.
Figure 18:
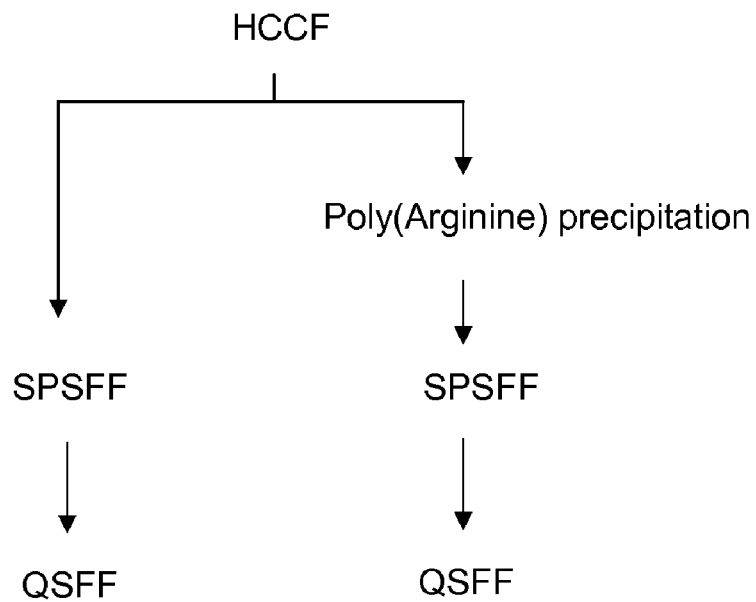
FIG. 18 shows the same process for the purification of the rhuMab 2H7 antibody from harvested cell culture fluid (HCCF) as FIG. 17, with elimination of the Prosep vA step: left column—SPSFF then QSFF; right column—polyarginine precipitation, SPSFF, then QSFF.
Figure 19:
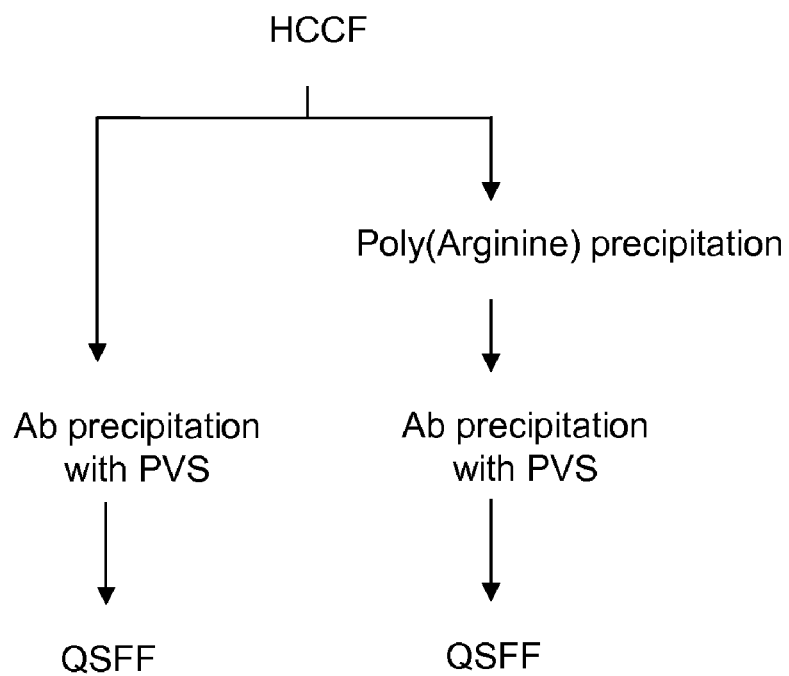
FIG. 19 shows process steps for the purification of the rhuMab 2H7 antibody from harvested cell culture fluid (HCCF) followed by: left column—antibody precipitation with PVS then QSFF; right column—polyarginine precipitation, antibody precipitation with PVS, then QSFF.

Solubility curves were generated for anti-cMet over a range of pH and select ionic strengths due to limited material availability. Solubility curves were generated from protein A pool adjusted to pH 4-pH 7 (FIG. 15). These curves were used to select the pH, ionic strength and PVS concentration at which the preparative scale precipitations would be performed. At pH 4 and conductivity of 2 mS/cm anti-cMet fully precipitated from solution at PVS:Ab mol ratio greater than 40 (FIG. 15). At pH 5, solubility curves were obtained at conductivities of 1 mS/cm and 2.4 mS/cm. At the higher conductivity anti-cMet did not fully precipitate from solution. By lowering the solution conductivity to 1 mS/cm, anti-cMet more readily precipitated from solution. At this conductivity maximum precipitation occurred at PVS:Ab mol ratios of 100. At mol ratios greater than 100 the polyelectrolyte complex had increased solubility, likely due to polyelectrolyte charge-charge repulsion effects. A comparison of the solubility curves at pH 4 and pH 5, conductivity of ~2 mS/cm suggest that electrostatic shielding effects by solution counter ions influences the pH at which bulk phase separation occurs and that a decrease in solution ionic strength is necessary with increased pH. At pH 6 and pH 7 and solution conductivities of 0.5 mS/cm, anti-cMet did not fully precipitate from solution over the concentrations of PVS tested. A maximum precipitation of 21% (C/Co=0.79) and 12% (C/Co=0.88) occurred at pH 6 and pH 7 respectively. The solubility curve of anti-cMet at pH 6 and pH 7 is markedly different compared to full length humanized antibodies with a similar protein pI, 8.3. For example, using similar conditions, pH 7.0 and a solution of conductivity 0.7 mS/cm, Apomab fully precipitates (C/Co=0) with same R values used in these experiments.

A purification process for anti-cMet (pI 8.3, 100 kDa) with PVS precipitation was compared with a standard process using four chromatography steps, a protein A capture step followed by two cation exchange steps run in bind and elute mode and finally a hydrophobic interaction chromatography step operated in flow through mode (Table 7). Both cation exchange steps and the hydrophobic interaction step were replaced with a PVS precipitation followed by anion exchange chromatography run in flow through mode. At pH 4, the precipitation reaction could be performed at higher ionic strengths. However, precipitating at pH 5 may give greater impurity clearance as more host cell impurities should be negatively charged at this pH and therefore stay in solution. Conditions of pH 5.0, conductivity of 0.6 mS/cm and PVS mol ratio of 100 (0.1% w/v) were selected to maximize antibody precipitation as determined from the solubility curves. The recovery yield for PVS precipitation of anti-cMet was affected by the solubilization of the PVS:antibody pellet. The PVS:antibody pellet was gel-like and difficult to solubilize. After solubilization of the pellet in QSFF equilibration buffer, the solution was hazy with particulates. The solution was easily filtered using a 0.4 µM vacuum filter, affording a clear solution that was processed over Q-Sepharose anion exchange chromatography.

The PVS precipitation step, conducted at pH 5, 0.5 mS/cm, and 0.1% PVS (w/v), reduced ECP to similar levels as the CM-Sepharose step (Table 7). Through the precipitation process, a significant decrease in leached protein A or an increase in % monomer was not observed.

TABLE 7

Summary of anti-CMet downstream processing results

| | Load Density (mg/ml) | Yield (%) | ECP (ng/mg) | Protein A (ng/mg) | Monomer (%) |
|---|---|---|---|---|---|
| Standard Process | | | | | |
| Protein A | 10 | 95 | 2000 | 40 | ND |
| CM Sepharose | 30 | 85 | 500 | 7 | ND |
| Poros 50 HS | 40 | 93 | 300 | <2 | ND |
| Phenyl Sepharose HS | 50 | 75 | 150 | <2 | 99 |
| Precipitation Process | | | | | |
| Protein A | 10 | 95 | 3000 | 40 | ND |
| PVS Precipitation* | N/A | 80 | 1988 | N/D | ND |
| QSFF | 40 | 95 | 666 | 38 | 93 |

Selection of Filtration Conditions for Capture of the Precipitate

Depth filters having adsorbent filter media particularly suited for removal of biological contaminants in cell culture fluid may be used in the methods of the invention. Depth filters are typically used in the production of biopharmaceuticals, as derived from mammalian cell culture, for the purpose of clarifying various crude product fluids. Cellulosic depth filters, such as MILLISTAK+® filters commercially available from Millipore Corporation, have a porous fixed bed of adsorbent material, such as a granular adsorbent, encased in a water-insoluble thermoplastic binder. The resulting composite filter allows for a higher amount of adsorbent with smaller adsorbent particles than conventional depth filters. These composite filters include a layer of tightly structured cellulosic depth media, and can be optimized to a specific application, such as retaining colloidal particles and cell debris or retaining whole cells and larger debris. They combine sequential grades of media, for example by stacked membranes, in a single filter cartridge. Such depth filters may be used in polishing or secondary clarification processes to remove small quantities of suspended matter from aqueous product (protein) streams. The filters may also protect or extend the service life of more expensive downstream separation processes, such as sterile filtration and affinity chromatography by removing colloidal contaminants and other cell debris. In addition, such depth filters are also useful for the protection of viral clearance filters by removing trace quantities of agglomerated proteins.

Certain depth filters also can retain, to varying degrees, some soluble contaminants commonly found in mammalian cell cultures, such as nucleic acids, host cell proteins, lipids, surfactants, etc. This retention capability for certain soluble contaminants is based on the adsorptive properties of the depth filter media. Filter media typically employed in depth filters includes refined cellulose fibers (wood pulp and/or cotton derived), diatomaceous earth, or water-soluble thermoset resin binders (U.S. 2007/0193938). The diatomaceous earth (a natural form of silica containing trace amounts of various silicates) in these composites is typically 40-60% by weight, adsorbing colloidal size biological matter such as cell fragments, organelles and agglomerated proteins, as well as various soluble biochemicals such as proteins, lipids and nucleic acids (DNA and RNA).

Depth filtration was evaluated as a capture step for PVS antibody precipitate. The wide size distribution of the precipitate presents a challenge for capturing the precipitate using filtration. Each filter media was tested with precipitated antibody under normal flow filtration conditions. Depth filtration media with varying pore sizes were screened for their ability to fully capture the precipitate. The optimal filter media was selected based on its ability to fully capture the precipitate and also for its ability to be loaded to a high capacity. Vmax was used to assess pressure drop across the filter as well as to determine the maximum capacity. Table 8 shows the filtration media evaluated. The MILLISTAK+® CE (cellulose only) series of media evaluated include 20CE, 35CE and 45CE. The MILLISTAK+® HC (cellulose and inorganic filter aid) series of media evaluated include C0HC, B1HC and A1HC (Rathore et al (Aug. 1, 2004) BioPharm Intl.; U.S. 2007/0193938). MILLISTAK® filter cartridges and sheets are available from the Millipore Corp. (Bedford, Mass.).

As shown in Table 8, the 20CE media is more open compared to the 35CE and 45CE. The 20CE contains a nominal pore size range of 5-10 microns whereas the 35CE and 45CE contain nominal pore sizes of 2-4 microns and 0.8-2 microns respectively. These series of filter media were selected to narrow down a range of pore sizes which enable complete capture of antibody (humanized 2H7 variant)-PVS precipitate. The 20CE media resulted in the capture of 45% of precipitate whereas the 35CE resulted in 48% of the precipitate being captured. In comparison, the 45CE resulted in the capture of 97% of the precipitate. The Millistak+ HC series of media is tighter than the Millistak+ CE series. The C0HC media has a nominal pore size range of 0.2-2 microns whereas the B1HC and A1HC have tighter pore sizes in the rage of 0.05-0.7 micron and 0.05-0.4 micron respectively. All three resulted in the capture of 99% of precipitate.

TABLE 8

| Filtration Media | Nominal Pore Size Range (μm) | % Antibody (2H7)-PVS Precipitate Capture |
| --- | --- | --- |
| CE20 | 5.0-10 | 45% |
| CE35 | 2.0-4.0 | 48% |
| CE45 | 0.8-2.0 | 97% |
| C0HC | 0.2-2.0 | >99% |
| B1HC | 0.05-0.7 | >99% |
| A1HC | 0.05-0.4 | >99% |

Figure 34:
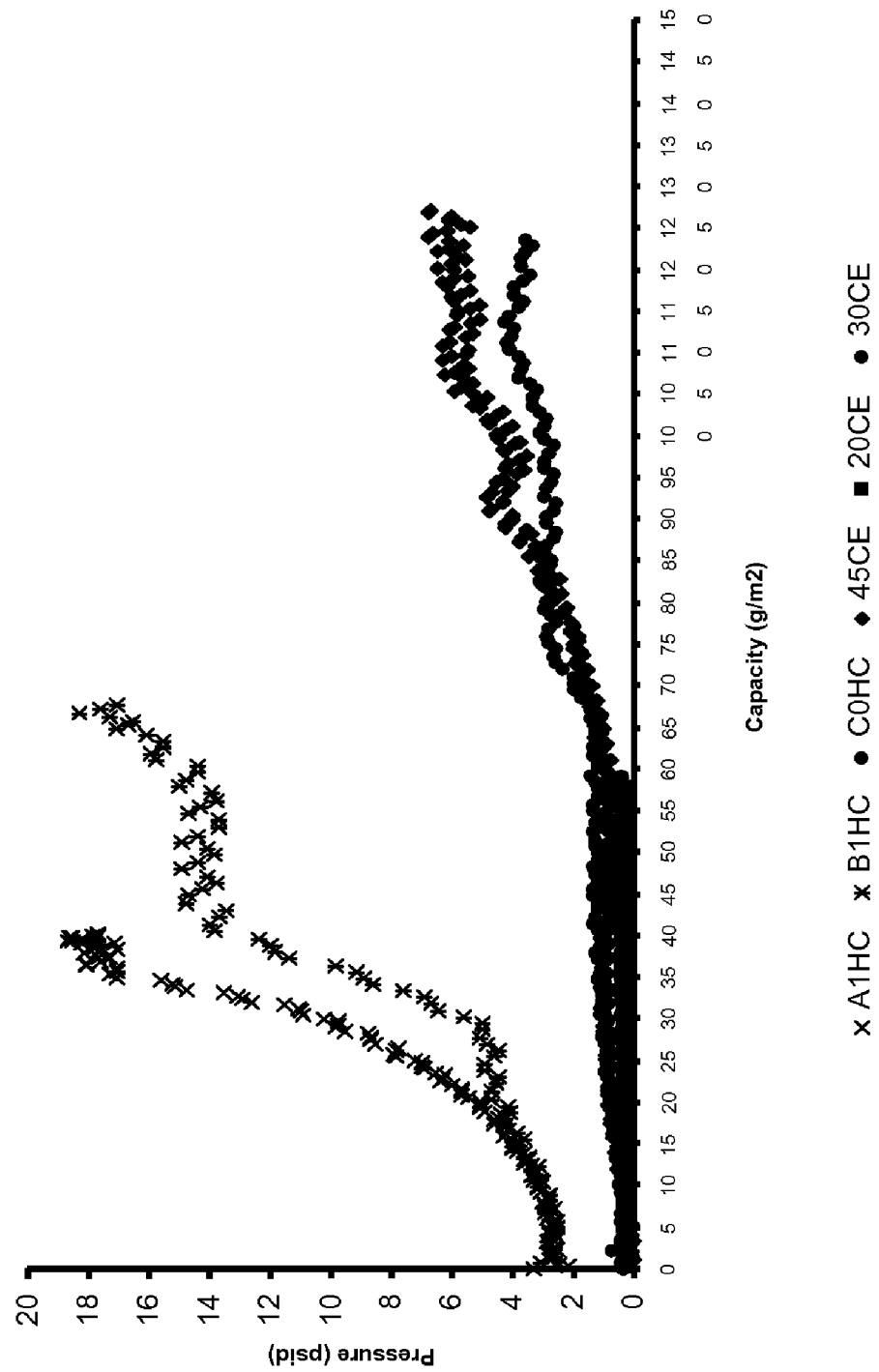
FIG. 34 shows a Vmax plot of capacity (measured in gram of antibody per filter area) versus pressure drop for each filter media: A1HC, B1HC, C0HC, 45CE, 20CE, 30CE.

FIG. 34 shows a Vmax plot of capacity (measured in gram of antibody (2H7) per filter area) versus pressure drop for each filter media (Table 8). A pressure limit of 17 psi was set to indicate the end of experiment due to filter fouling. A target capacity of 125 g/m$^2$ was set to indicate end of experiment in the event of no filter fouling. Both A1HC and B1HC filter media reached 17 psi and thus provided the lowest capacity. Capacity at the end of filtration using A1HC media was 40 g/m$^2$ whereas the capacity at the end of filtration using B1HC media was 68 g/m$^2$. C0HC reached the end capacity of 125 g/m$^2$ with a maximum pressure of 3.5 psi. As mentioned above, 20CE and 30CE retained less than 50% of precipitate and were therefore not taken to the target capacity. 45CE reached the target capacity with a maximum pressure of 7 psi.

Selection of Resolubilization Conditions for Resolubilization of the Precipitate within a Depth Filter A number of resolubilization methods were evaluated to recover captured antibody from the depth filter. The goal for this step was to develop a robust method with high antibody recovery. The first method evaluated was the resolubilization of antibody from precipitate using a high conductivity buffer at a high pH. Under high pH and conductivity conditions, the antibody is less positive and more ions in solution shield the PVS and antibody thereby preventing precipitation. A 50 mM Tris base/50 mM sodium acetate buffer at pH's in the range of 8-8.5 and conductivity of ~6 mS/cm was used to resolubilize the antibody. The buffer was flushed through the depth filter and the resulting pool contained antibody and PVS. Variables such as flow rate and volume of buffer needed to completely resolubilize the antibody were evaluated. Recirculation of buffer through the depth filter was also evaluated as a method of generating a more concentrated pool.

Figure 35:
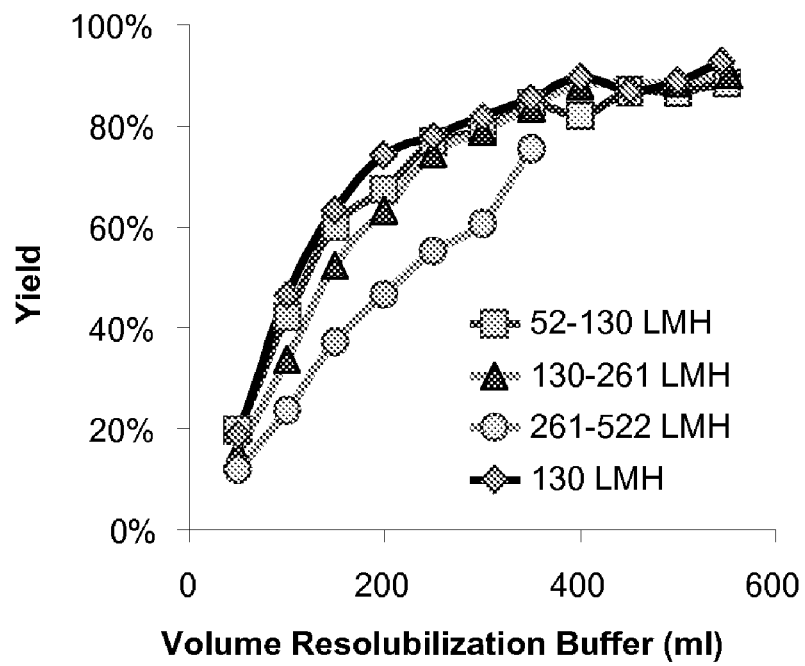
FIG. 35 shows the effect of varying flow rate through on yield in terms of volume of buffer necessary to reach complete resolubilization of the 2H7-PVS protein-polyelectrolyte precipitate from the C0HC MILLISTAK+® filter media. LMH=liters per square meter per hour, a flow rate measurement.

FIG. 35 shows the effect of varying flow rate on yield in terms of volume of buffer necessary to reach complete resolubilization of the 2H7-PVS protein-polyelectrolyte precipitate from the C0HC MILLISTAK+® filter media. Fluxes in the range of 52-130 LMH (liters per square meter per hour, a flow rate measurement) and 130-261 LMH show a similar trend with both curves resulting in similar final yields with 600 ml of buffer. The curve at a flux of 130 LMH encompasses the same trend and also results in a similar yield with 600 ml of buffer. Varying the flow rate did not improve the yield to buffer volume ratio. The highest antibody concentration obtained using this method was 1 g/L.

Figure 36:
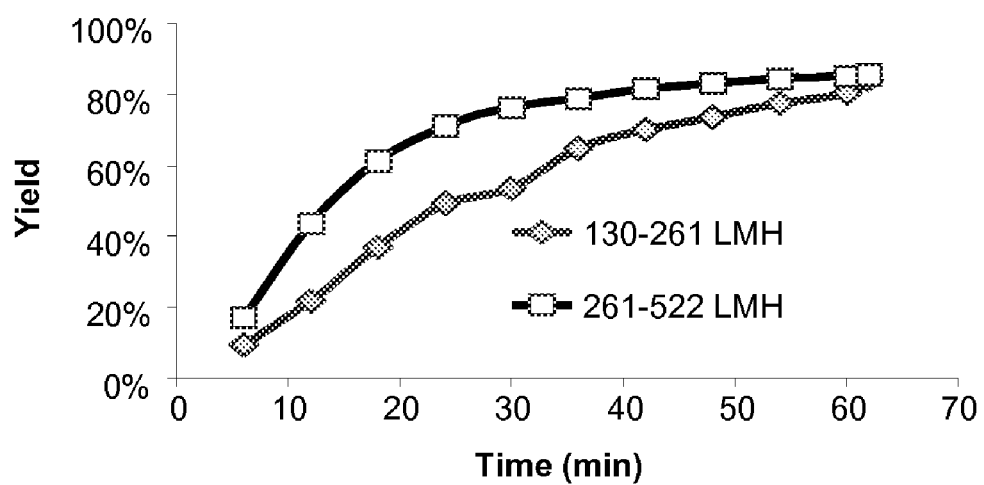
FIG. 36 shows the effects of two ranges of flux (flow of resolubilizing buffer in LMH) on resolubilization of protein from the C0HC MILLISTAK+® filter (2H7-PVS protein-polyelectrolyte precipitate).

Recirculation of the buffer through the depth filter was evaluated as a method which could potentially result in a more concentrated pool. A reservoir containing buffer served as both the inlet buffer and outlet pool container. As shown in FIG. 36, two ranges of flux (flow of resolubilizing buffer in LMH) were tested to determine optimal processing time in which we recover the majority of our protein from the filter as the 2H7-PVS protein-polyelectrolyte precipitate. A flux in the range of 130-261 LMH reached the same yield of 84% as the flux in the range of 261-522 LMH after 60 minutes. In terms of pool concentration, the recirculation method resulted in a more concentrated pool when compared to a single pass of buffer through the depth filter. The highest antibody concentration obtained using the recirculation method was 2 g/L.

Figure 37:
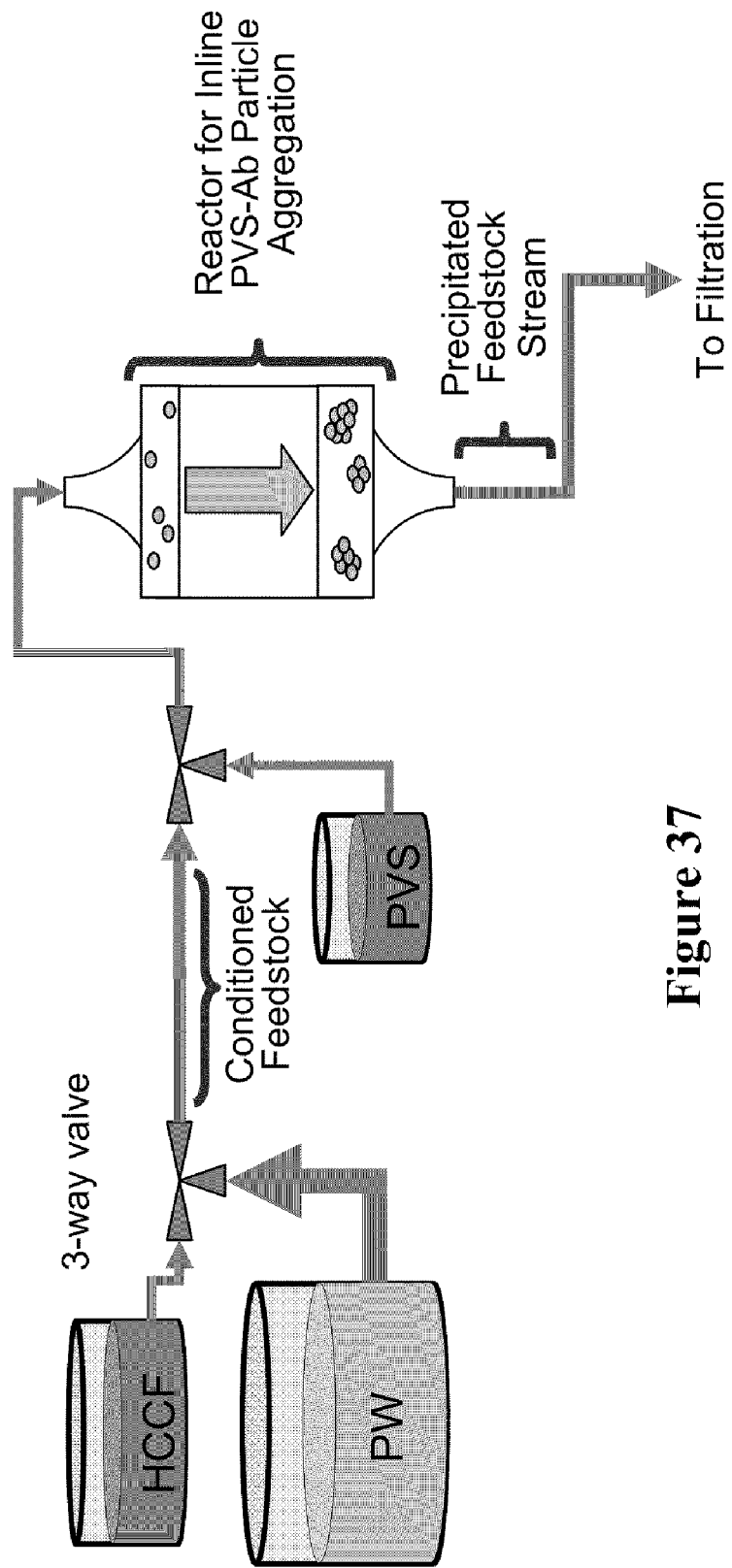
FIG. 37 shows a process schematic of inline HCCF conditioning/PVS precipitation setup

Operation of the Precipitation Reaction and Depth Filtration Capture in Continuous Mode PVS precipitation relies upon the ionic interaction between the strongly anionic PVS molecule and only slightly cationic antibody molecules in solution. Diluting protein feedstocks to lower the conductivity of the solution to an acceptable range for PVS precipitation can cause large increases in feedstock volume. To avoid possible volume restrictions at manufacturing scale, it is necessary to develop a scheme for conditioning feedstock inline. Inline dilution can be used to lower the conductivity of a feedstock stream without requiring a tank for mixing. By merging a PVS stream with the conditioned feedstock stream, PVS-antibody precipitation can occur inline and eliminate the need for a large precipitation tank at scale. FIG. 37 depicts an outline of an inline HCCF conditioning/PVS precipitation setup with objectives of: (i) long residence time and low fluid velocity to promote PVS-MAb particle aggregation; (ii) large cross-sectional area of inline reactor to maintain high process throughput; and (iii) lab-scale implementation.

While PVS-antibody precipitation may occur readily upon inline mixing of PVS and conditioned feedstock streams, the PVS-antibody precipitate particle aggregation process is very sensitive to stream turbulence, dwell time, and average linear fluid velocity. A period of low agitation dwell time is required for the sample particle aggregation required to form precipitate particles large enough to be captured by filtration media. High stream velocity may prevent PVS-Ab precipitate from forming larger aggregate, creating a stream of very small precipitate particles which may be difficult to capture by filtration media.

Figure 38:
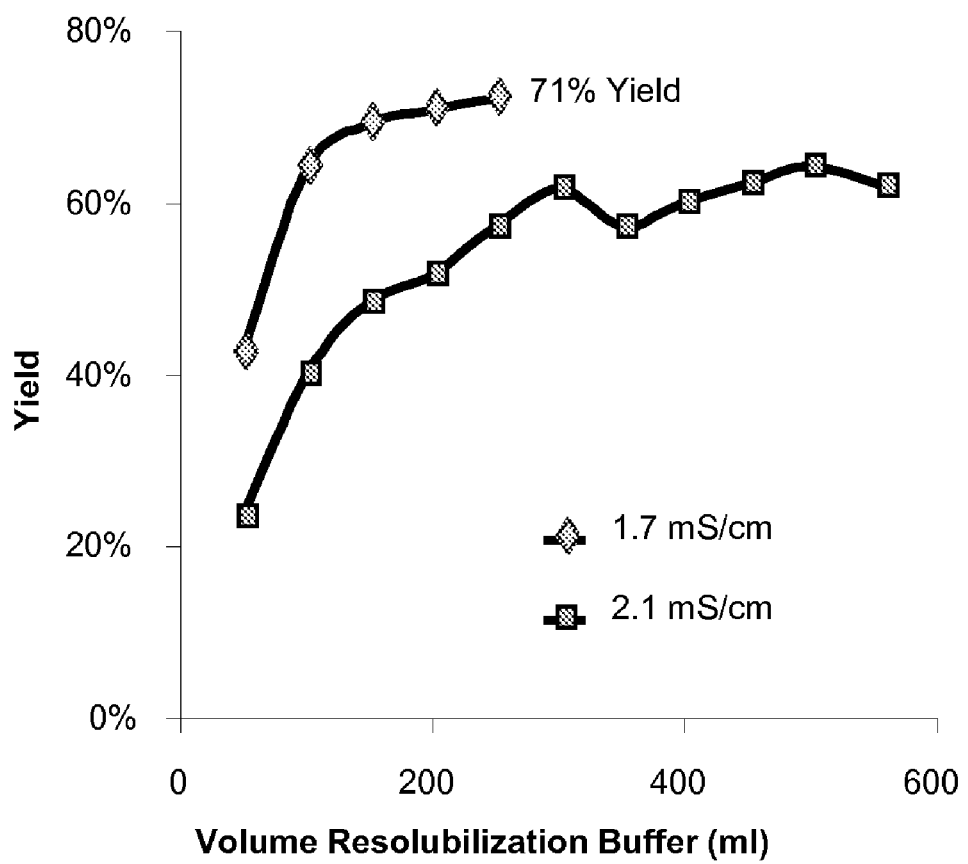
FIG. 38 shows antibody recovery yields continuous feedstock conditioning/precipitation.

An inline, continuous feedstock conditioning/PVS precipitation pipeline is provided at lab-scale in conjunction with a depth filtration capture method that processes the continuously precipitated feedstock stream. Antibody recovery yields ranging from 71%-60% have been observed (FIG. 38 for antibody yield plots) with the process schematic shown in FIG. 37 with 9-fold CHOP clearance over the inline PVS precipitation step.

Selection of Cationic Polyelectrolyte Precipitation Conditions

Solubility curves were generated using two molecular weights of polyarginine (Poly-L-Arginine) in CCF and HCCF. Solubility curves are a plot of residual protein left in the supernatant following precipitation (expressed as a percentage) versus concentration of polyelectrolyte expressed as weight of polyelectrolyte (g)/volume of solution (mL).

Figure 20:
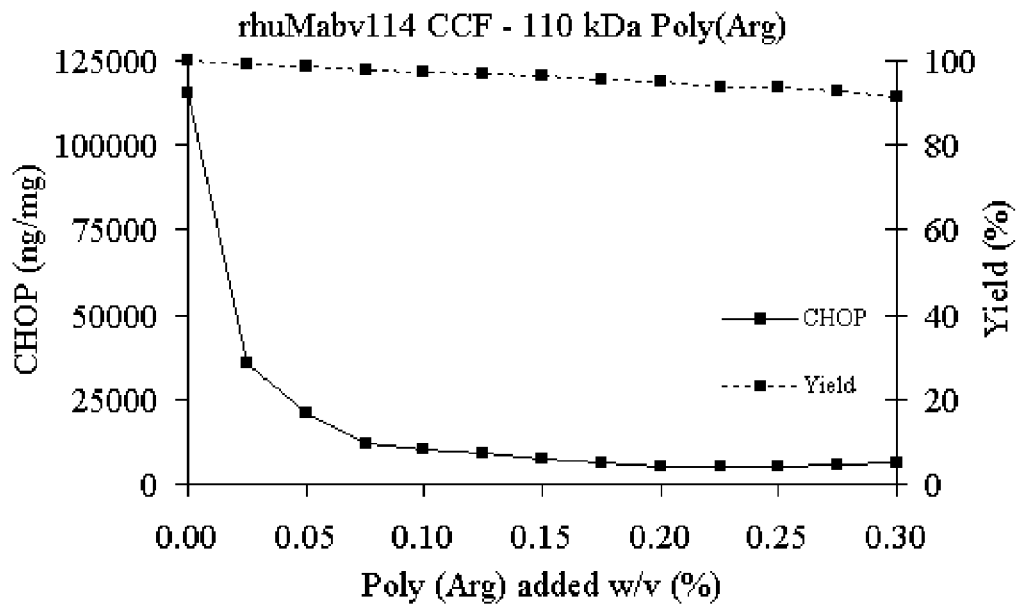
FIG. 20 shows a rhuMab 2H7 CCF solubility curve with 110 kDa polyarginine
Figure 21:
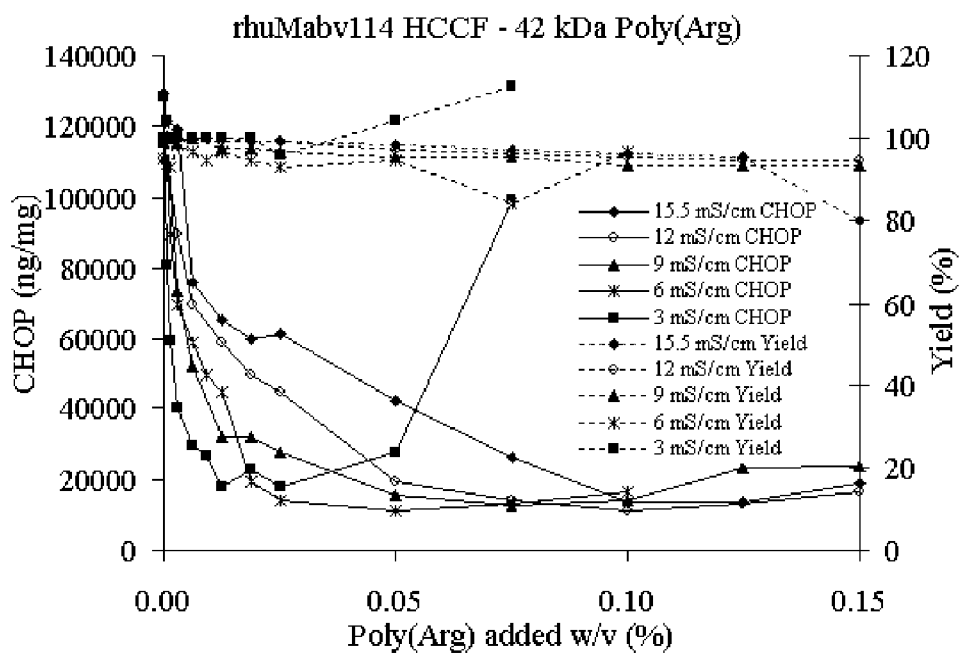
FIG. 21 shows rhuMab 2H7 HCCF solubility curves—42 kDa polyarginine
Figure 22:
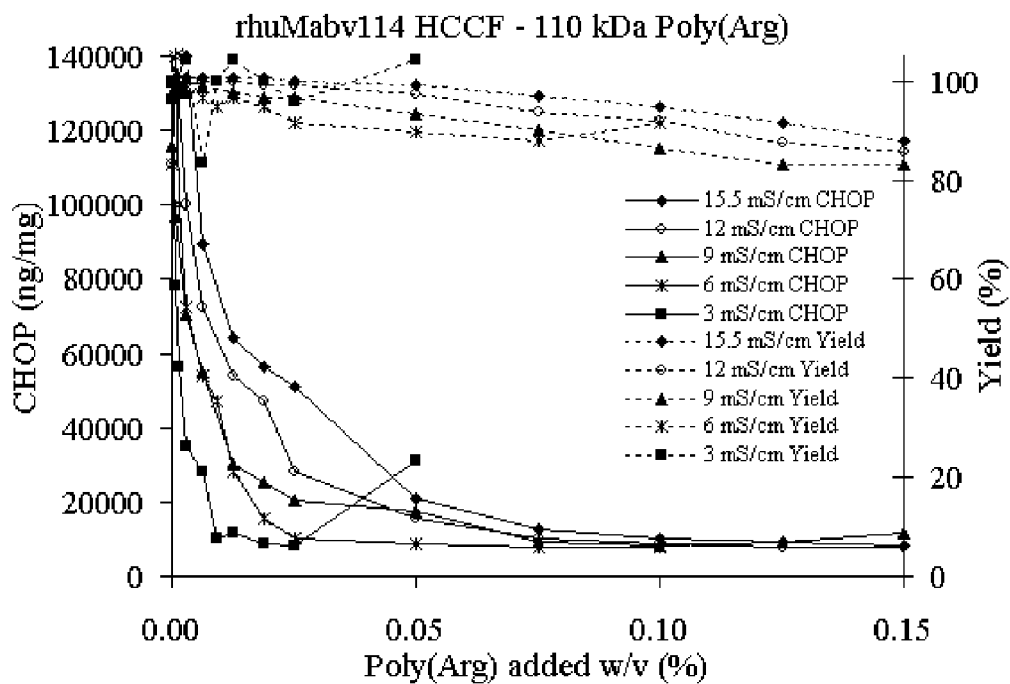
FIG. 22 shows rhuMab 2H7 HCCF solubility curves—110 kDa polyarginine

Solubility curves were generated for rhuMab $2H_7$ CCF (FIG. 20) and HCCF (usually at pH 7) for a range of ionic strengths (FIGS. 21 and 22). These curves were used to select optimum CHOP precipitation conditions at which preparative scale precipitations would be performed namely the ionic strength, polyarginine concentration and molecular weight. Solubility curves were also generated with anti-CD22 and rhuMab C2B8 HCCF (FIGS. 23 and 24) to ensure robustness and consistency of precipitation technique. To evaluate the feasibility of antibody purification through two precipitation steps, cationic polyelectrolyte precipitation followed by anionic polyelectrolyte precipitation, solubility curves were generated for PVS precipitation of rhuMab HCCF generated from the flocculation of CCF with 0.075% w/v 110 kDa polyarginine (FIG. 25). With increasing polyarginine concentration, there was CHOP precipitation, as indicated by a decrease in residual CHOP (ng/mg) in the supernatant. Optimum CHOP precipitation occurred at 0.2% w/v concentration of polyarginine with a 22 fold reduction in CHOP, with a 95% yield. Further increase in polyarginine concentration did not result in a significant CHOP reduction, but there was a decrease in yield.

CHOP precipitation seems to be a function of ionic strength and molecular weight of the polyelectrolyte, as seen in rhuMab 2H7 HCCF solubility curves (FIGS. 21 and 22). With decreasing conductivity, there was an increase in precipitation. In general, increasing the molecular weight of the polyelectrolyte seemed to have an impact on CHOP precipitation. At similar concentrations of polyarginine, higher molecular weight polyelectrolyte (110 kDa) precipitated more CHOP compared to the lower molecular weight polyelectrolyte (42 kDa). At a particular conductivity (except 3 mS/cm), the addition of polyarginine greater than 0.1% w/v did not result in further significant CHOP reduction. At 0.1% w/v concentration of polyarginine, 10 fold and 13 fold CHOP reduction was obtained for 42 kDa and 110 kDa molecular weights respectively and the yields were >95% for both the molecular weights.

Figure 23:
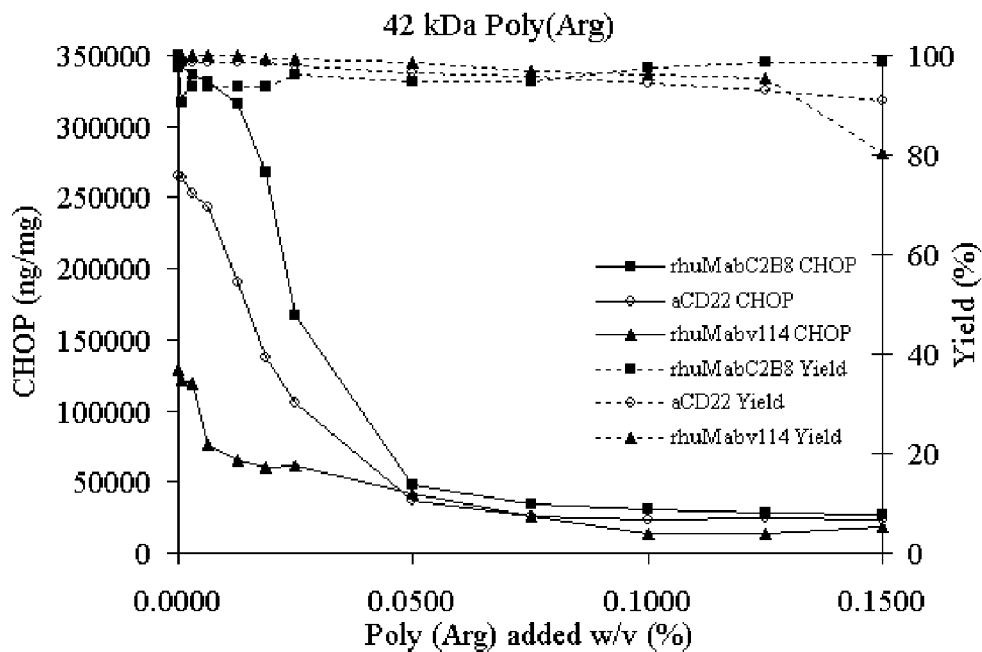
FIG. 23 shows rhuMab 2H7, anti-CD22, rhuMab C2B8 HCCF solubility curves—42 kDa polyarginine
Figure 24:
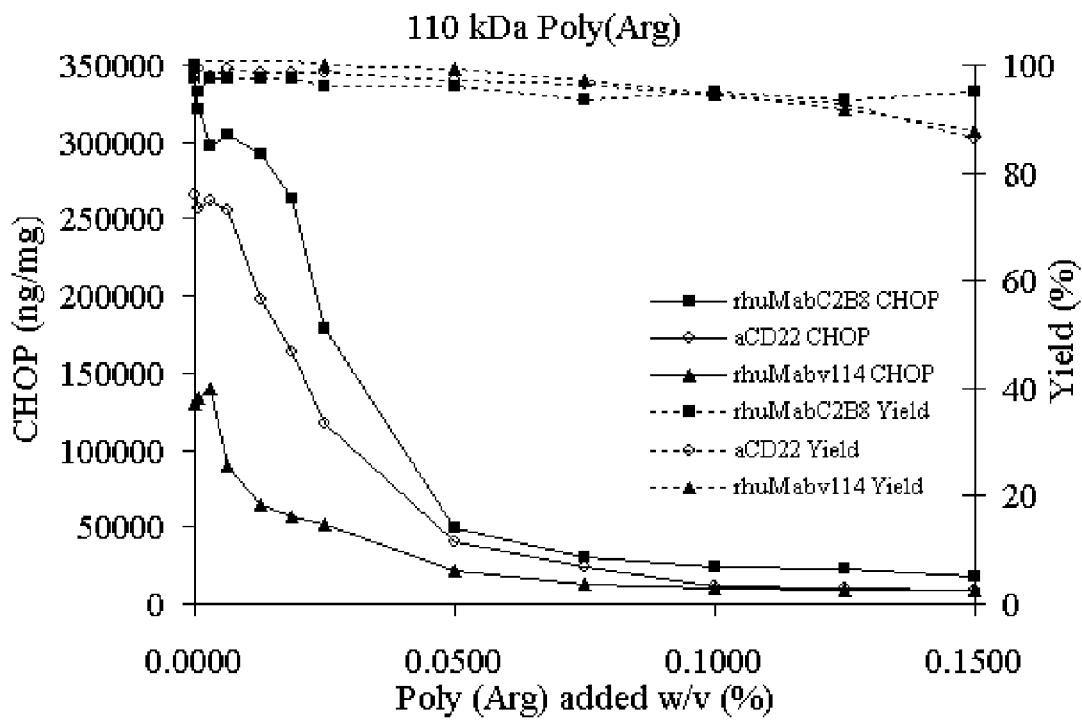
FIG. 24 shows rhuMab 2H7, anti-CD22, rhuMab C2B8 HCCF solubility curves—110 kDa polyarginine
Figure 25:
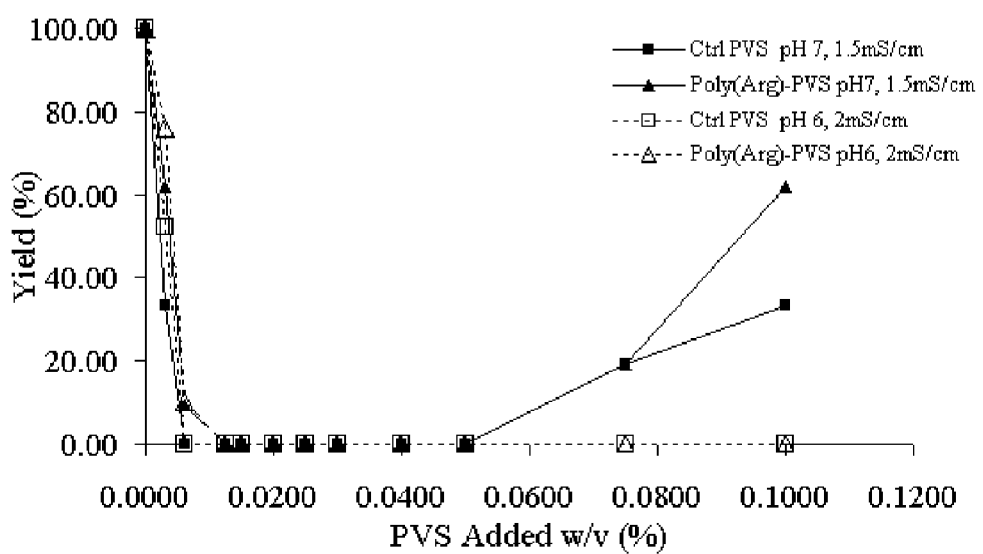
FIG. 25 shows solubility curves of PVS precipitation of rhuMab 2H7 CCF flocculated with 0.075% w/v 110 kDa polyarginine.

Similar trends were observed with the anti-CD22 and rhuMab C2B8 HCCF, as seen in rhuMab 2H7, anti-CD22, rhuMab C2B8 HCCF solubility curves (FIGS. 23 and 24). Precipitation of anti-CD22 HCCF with 0.1% w/v 110 kDa polyarginine resulted in 25 fold CHOP reduction and 95% yield. Optimum CHOP precipitation for rhuMab C2B8 occurred at a concentration of 0.15% w/v 110 kDa polyarginine, which resulted in 20 fold reduction in CHOP and 95% yield.

With increasing PVS concentration, there was complete precipitation of antibody in the feedstock flocculated with polyarginine at both the pH and conductivities tested, indicated by a decrease in yield (%) (FIG. 25). This indicates minimal interference of the presence of polyarginine on PVS precipitation of the antibody under the conditions tested. At pH 7 and 1.5 mS/cm conductivity, once a maximum level of precipitation was observed, the addition of additional PVS caused the precipitant to re-dissolve.

Downstream Processing of rhuMab 2H7

The standard process currently uses three chromatography steps, a protein A capture step followed by a cation and anion exchange step. Flocculating the CCF with 0.075% w/v 110 kDa polyarginine and processing the HCCF with antibody precipitation with PVS followed by QSFF step is shown as Process flow a), Table 9). The primary function of this flocculation step is to clarify the CCF by removing solids (cell debris), thereby reducing turbidity and to precipitate host cell impurities such as CHOP and DNA. Polyarginine was able to flocculate the solids and the cell culture media components, and reduced CHOP to 23480 ng/mg (4 fold reduction) and completely removed DNA. If the concentration of 110 kDa polyarginine was increased to 0.2% w/v, up to 22 fold CHOP reduction as indicated by the solubility curves (FIG. 20) was obtained. PVS precipitation of flocculated HCCF further reduced CHOP to 212 ng/mg, which was significantly less than CHOP in control HCCF-PVS pools. Control HCCF-PVS-Q pools had nearly twice the amount of CHOP as the Poly(Arg) HCCF-PVS-Q pools. The DNA assay does not function in the presence of PVS so PVS clearance across the precipitation step cannot be assessed. The yields across all the steps were greater than 95% except the PVS precipitation steps (Table 9). These low yields for PVS steps can be attributed the precipitation procedure and handling at preparative scale as opposed to the mechanism and conditions of precipitation (FIG. 25). The percent monomer by SEC, Insulin and Gentamicin were not evaluated for these pools.

Figure 26:
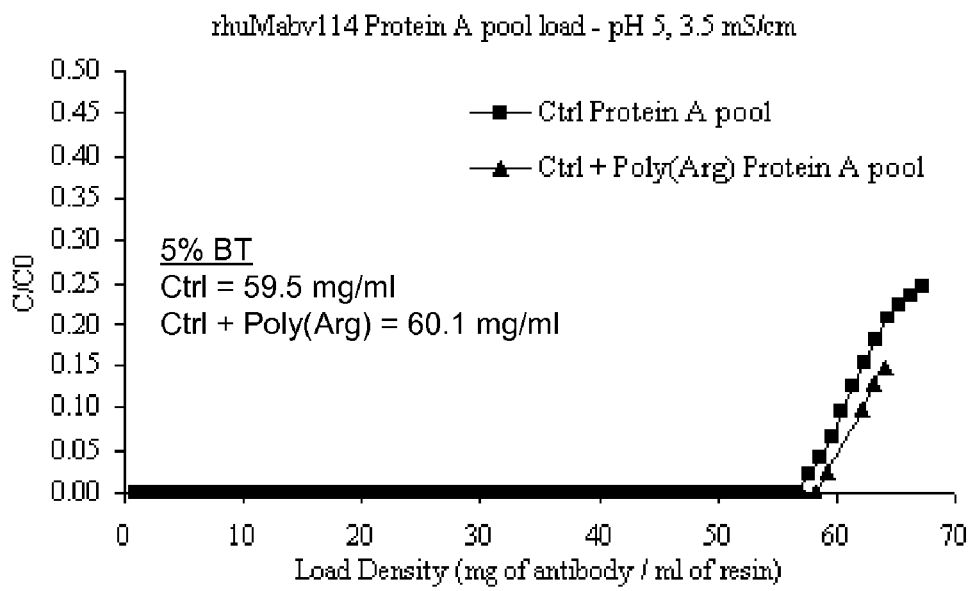
FIG. 26 shows breakthrough curves of SPSFF with Protein A pool generated from polyarginine precipitated HCCF as load.
Figure 27:
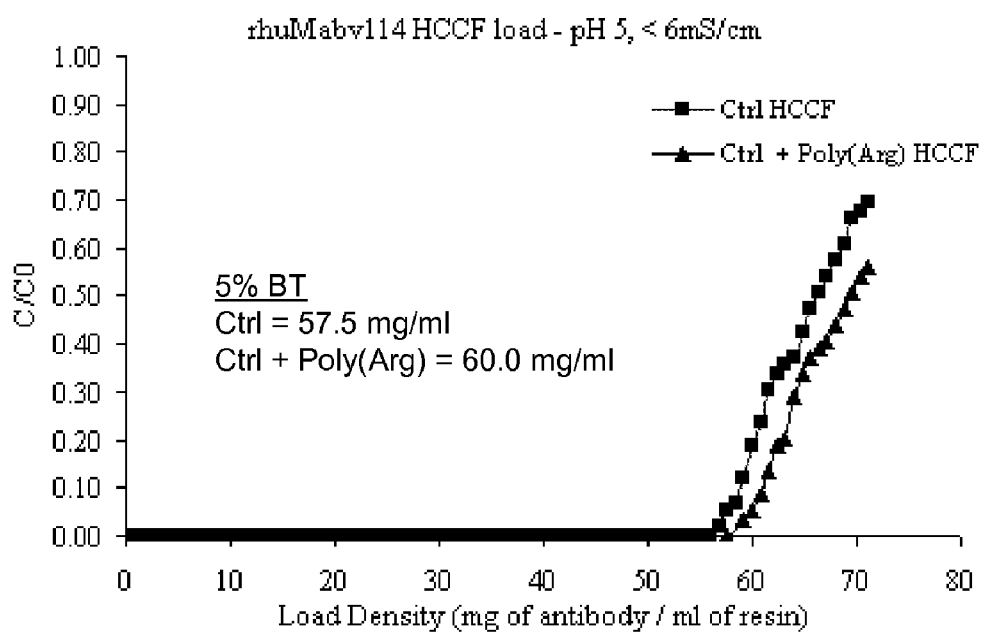
FIG. 27 shows breakthrough curves of SPSFF with HCCF generated from polyarginine precipitated as load.

In order to study the impact on downstream processes, HCCF was precipitated with 0.1% w/v 110 kDa polyarginine and taken through various purification schemes. The yield for the antibody was 97% and CHOP was reduced by 18 fold and DNA was completely removed by polyarginine precipitation. Insulin and Gentamicin was not cleared by this precipitation step. Prior to processing the precipitated HCCF downstream, breakthrough curves were generated to evaluate the impact of polyarginine on the SPSFF resin's load capacity. For both loads, polyarginine precipitated HCCF and post precipitation protein A pool, 5% breakthrough on SPSFF occurred at 60 mg of antibody per ml of resin similar to the control (without polyarginine precipitation). This indicates that polyarginine did not negatively impact the binding capacity of SPSFF (FIGS. 26 and 27).

Standard antibody process (Process flow b), Table 9): Polyarginine precipitated HCCF was processed across Protein A followed by ion exchange chromatography. The polyarginine-Protein A pool had CHOP levels similar to control Protein A, even though the CHOP levels in the load feedstocks were very different. Gentamicin and insulin were reduced to low levels by a Protein A step. CHOP was reduced 490 fold to 3 ng/mg over the SPSFF compared to 307 ng/mg in the absence of precipitation step. DNA, Leached protein A, Insulin and Gentamicin were also reduced to acceptable levels by polyarginine-Protein A-SP process comparable to control process (Protein A-SPSFF-QSFF) (Table 9). Since the impurity levels are acceptable in SPSFF pools post polyarginine precipitation, it is not necessary to process them over QSFF.

Figure 28:
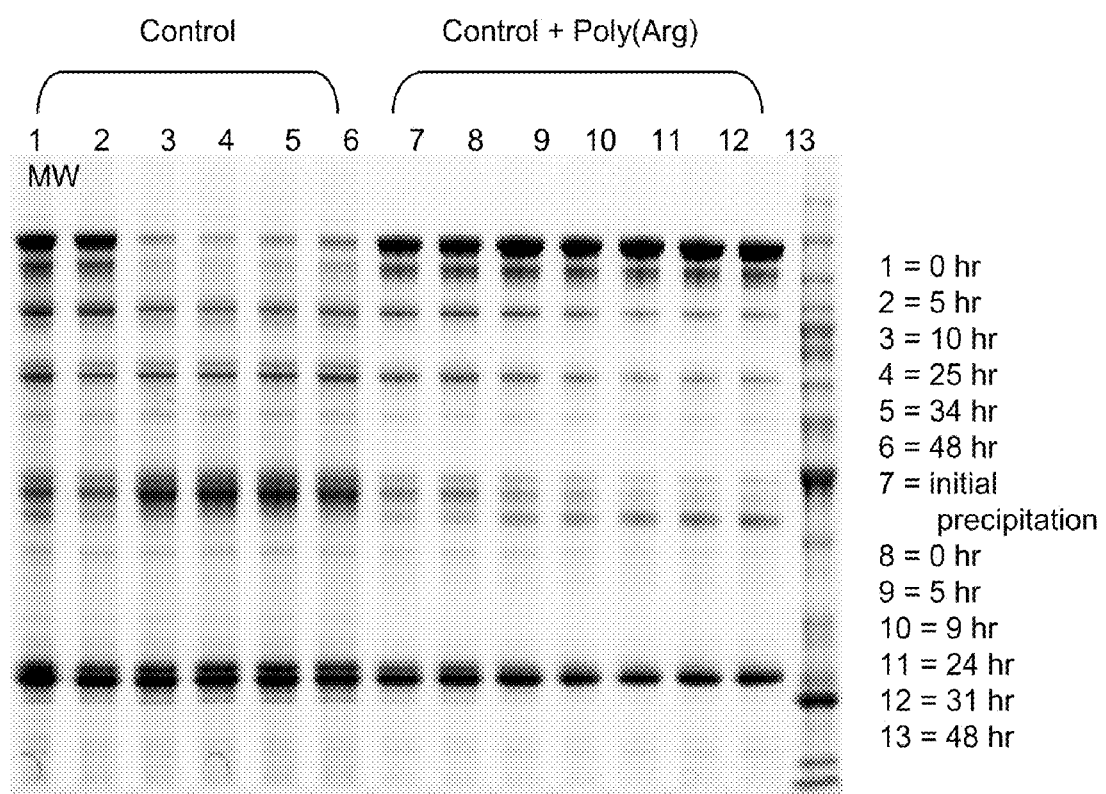
FIG. 28 shows gel electrophoresis of the inhibition of antibody reduction in 2H7 MAb. HCCF 4-12% BT, MOPS buffer, Sypro ruby stain, 2 ug HCCF load, 5 min. 70° C., 9 sec. exposure, 2 F/T Run 7, RT incubation in SS mini-cans, 500 µl (microliter) samples immediately frozen at −70° C.

Non affinity antibody purification process (Process flow c), Table 9): Polyarginine precipitated HCCF was processed across SPSFF followed by QSFF. Post precipitation SPSFF pool had 63 ng/mg of CHOP (76 fold reduction) compared to 6731 ng/mg in the absence of precipitation. The SPSFF completely removed Insulin and partially reduced Gentamicin. CHOP clearance was better in the polyarginine-SP process, while DNA, Insulin and Gentamicin clearance were comparable to control process (SPSFF-QSFF) (FIG. 28). After polyarginine precipitation, the CHOP levels in the SPSFF pool are similar to QSFF pool, suggesting that QSFF step is redundant in this process.

Two Step Precipitation/Chromatography Purification Process

Polyarginine precipitated HCCF was followed by antibody precipitation by PVS and then processed over QSFF (Process flow d, Table 9). PVS pool had 49 ng/mg of CHOP (99 fold reduction) compared to 1517 ng/mg in the absence of polyarginine precipitation. The PVS precipitation step completely removed Insulin and partially reduced Gentamicin. CHOP clearance was better in the polyarginine-PVS process, while DNA and Insulin clearance were comparable to control process (SPSFF-QSFF). Gentamicin clearance was 2 fold less in the control process, in the presence of QSFF step. After polyarginine precipitation, the CHOP levels in the SPSFF pool are similar to QSFF pool, suggesting that QSFF step is redundant in this process.

TABLE 9

Summary of downstream processing results for rhuMab 2H7

| | Yield (%) | CHOP (ng/mg) | SEC (% monomer) | Protein A (ng/mg) | DNA (pg/mg) | Insulin (ng/mg) | Gentamicin (ng/mg) |
|---|---|---|---|---|---|---|---|
| a) Control HCCF | NA | 93191 | ND | NA | 914893 | ND | ND |
| Poly(Arg) flocculated and harvested CCF | 97 | 23480 | ND | NA | <0.4 | ND | ND |
| Control HCCF-PVS | 80 | 900 | ND | NA | ND | ND | ND |
| Poly(Arg) flocculated and harvested CCF-PVS | 75 | 212 | ND | NA | ND | ND | ND |
| Control HCCF-PVS-Q* | 100 | 90 | ND | NA | ND | ND | ND |
| Poly(Arg) flocculated and harvested CCF-PVS-Q* | 100 | 54 | ND | NA | ND | ND | ND |
| b) HCCF | NA | 86331 | NA | NA | 373247 | 1.70 | 20500 |
| Poly(Arg) HCCF | 90 | 4836 | NA | NA | <0.3 | <1.93 | 22100 |
| HCCF-Pro A | 99 | 1689 | 98.1 | 9.3 | 52 | <0.01 | 33.9 |
| Poly(Arg) HCCF-Pro A | 103 | 1447 | 97.5 | 16.7 | <0.3 | 0.16 | 24.4 |
| HCCF-Pro A-SP | 100 | 307 | 98.4 | <2 | <0.2 | <0.02 | 1.2 |
| Poly(Arg) HCCF-Pro A-SP | 92 | 3 | 98.5 | <2 | <0.1 | <0.02 | 0.6 |
| HCCF-Pro A-SP-Q | 87 | <2.8 | 97.9 | <2 | <0.2 | <0.05 | 1.2 |
| Poly(Arg) HCCF-Pro A-SP-Q | 93 | <2.6 | 98.8 | <2 | <0.2 | <0.05 | 0.7 |
| c) HCCF-SP | 99 | 6731 | 97.6 | <2 | 0.7 | <0.02 | 99.9 |
| Poly(Arg) HCCF-SP | 88 | 63 | 98.8 | <2 | <0.2 | <0.02 | 84.3 |
| HCCF-SP-Q | 93 | 81 | 97.6 | <2 | <0.2 | <0.06 | 92.9 |
| Poly(Arg) HCCF-SP-Q | 99 | 46 | 98.3 | <2 | <0.2 | <0.05 | 81.1 |
| d) HCCF-PVS | 70 | 1517 | 97.0 | <2 | ND | <0.03 | 1030 |
| Poly(Arg) HCCF-PVS | 73 | 49 | 98.5 | <2 | ND | <0.03 | 1000 |
| HCCF-PVS-Q* | 97 | 79 | 97.2 | <2 | ND | <0.02 | 504 |
| Poly(Arg) HCCF-PVS-Q* | 98 | 34 | 98.6 | <2 | ND | <0.02 | 691 |

*Q loaded to 30 g/L; ND—Not Determined; NA—Not Applicable

Inhibition of Antibody Reduction

HCCF containing rhuMAb 2H7 was treated with polyarginine and held in stainless steel minicans for 48 hours, and samples were taken at regular time points and analyzed. The antibody was intact and not reduced over the entire time period in the polyarginine precipitated HCCF as opposed to the control where the antibody starts to reduce at 10 hours (FIG. 28). Polyarginine inhibits antibody-reducing agents by precipitating them along with other negatively charged impurities.

Evaluation of Other Cationic Polyelectrolytes

Optimization of precipitation conditions to further enhance the removal of impurities may include use of other polyelectrolytes as well as optimization of other conditions such as rate and type of agitation, and the rate of polyelectrolyte addition. Another basic poly(amino acid), polylysine, was selected for an initial comparison to polyarginine. Polyarginine has a guanidinium cation functional group giving it a pKa of approximately 12.5. Polylysine has an amine cation as functional group giving it a pKa of approximately 10.5. Both polyarginine and polylysine are commercially available in multiple molecular weights.

rhuMab C2B8 Protein A Pool Solubility Curve

Figure 29:
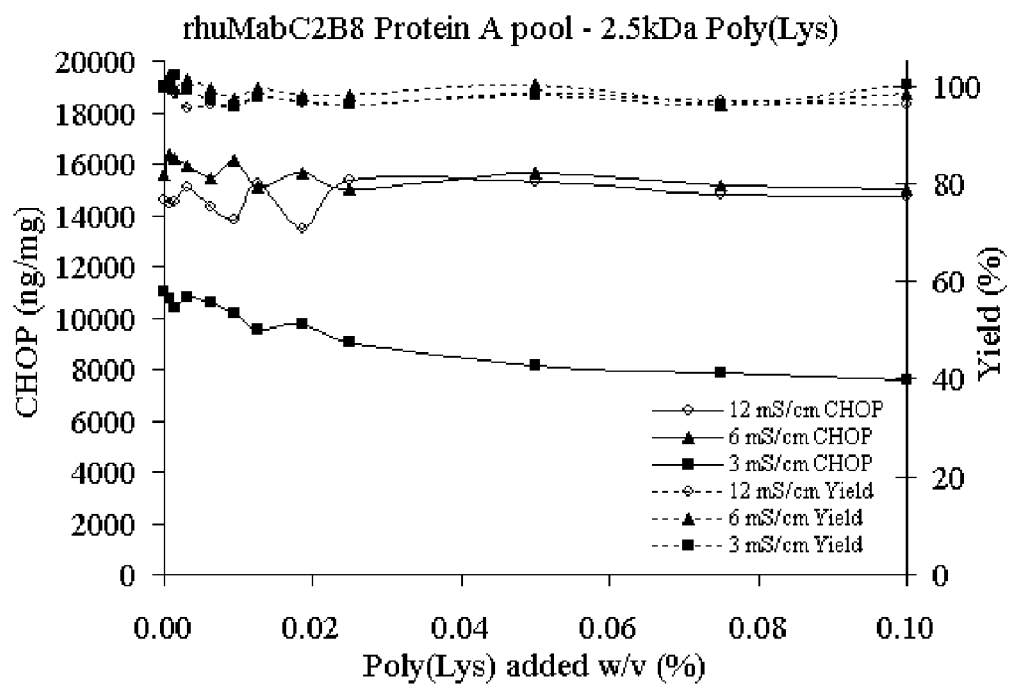
FIG. 29 shows rhuMab C2B8 protein A pool solubility curves—2.5 kDa polylysine
Figure 30:
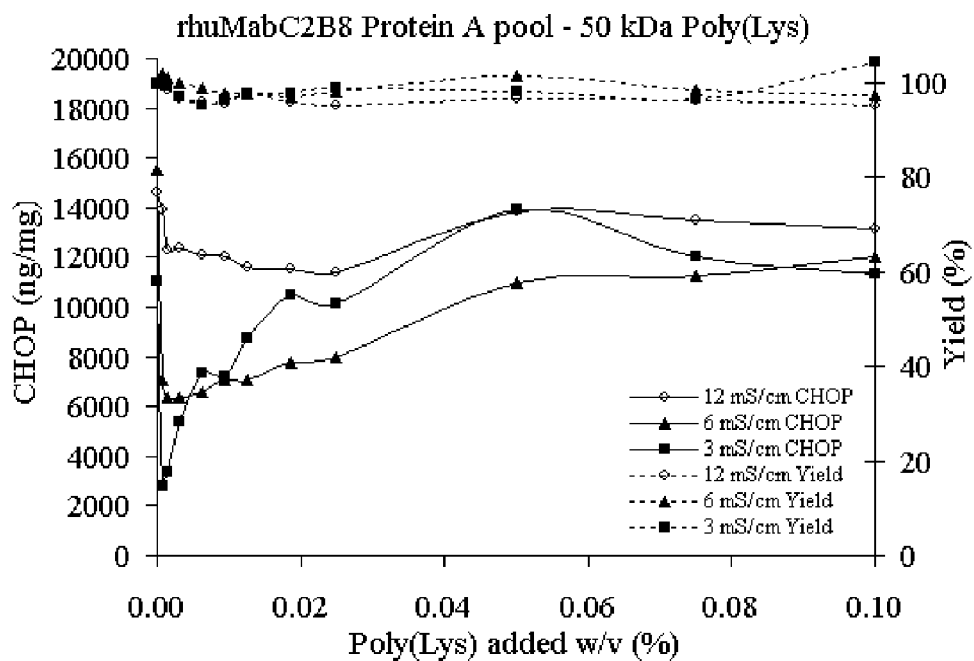
FIG. 30 shows rhuMab C2B8 protein A pool solubility curves—50 kDa polylysine

CHOP precipitation by the positively charged, polycation polyelectrolyte is correlated with ionic strength and molecular weight of the polyelectrolyte (FIGS. 29 and 30). Lower molecular weight polylysine (2.5 kDa) did not precipitate CHOP in the conductivity range 3-12 mS/cm. However 50 k Da polylysine resulted in 4 fold and 2 fold CHOP reductions at 3 mS/cm and 6 mS/cm respectively. No significant CHOP precipitation was observed at 12 mS/cm. In general, with decreasing conductivity, there was an increase in CHOP precipitation and increasing the molecular weight of the polyelectrolyte seemed to have an impact on CHOP precipitation. At lower conductivities, once maximum CHOP precipitation was obtained, further addition of polylysine resulted in resolubilization of the precipitate. Yields were greater than 95% for all conditions tested.

rhuMab C2B8 HCCF Pool Solubility Curve

Figure 31:
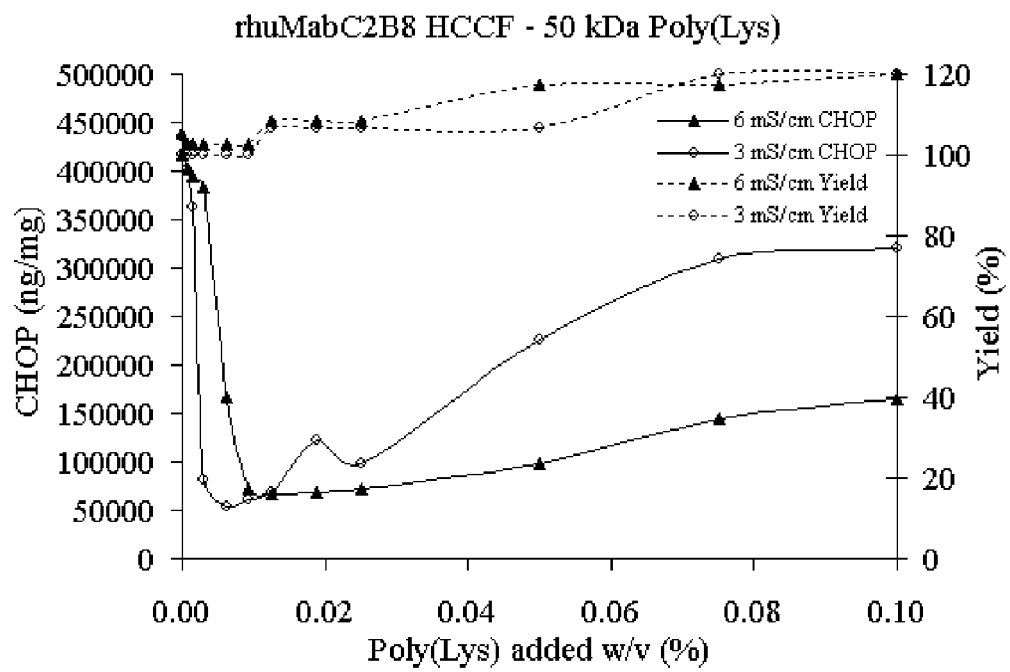
FIG. 31 shows rhuMab C2B8 HCCF solubility curves—50 kDa polylysine
Figure 32:
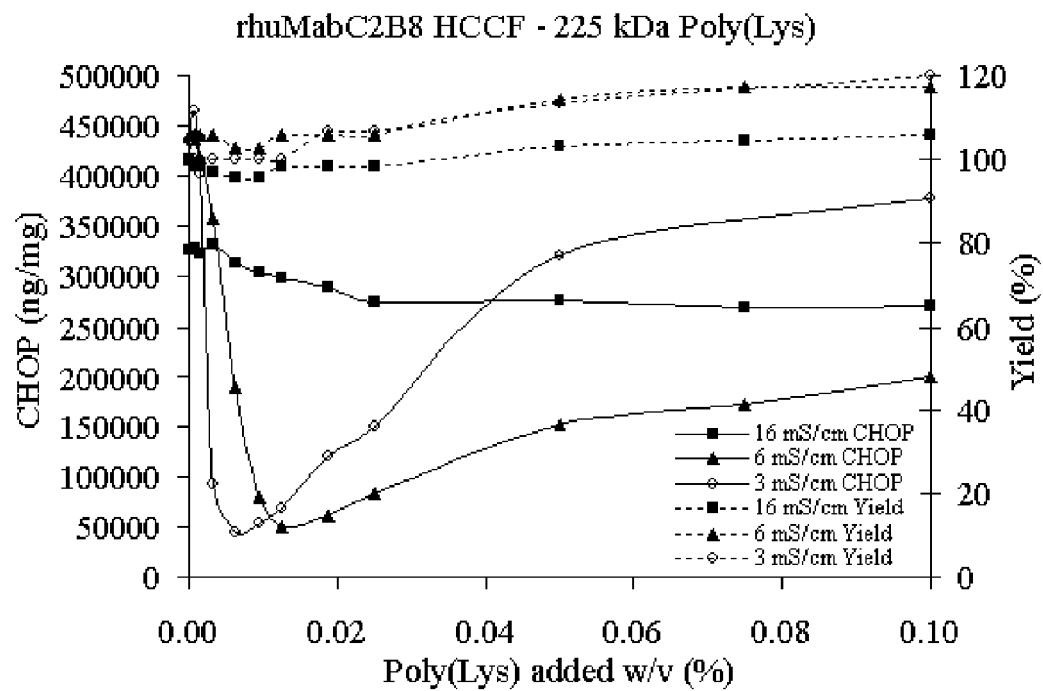
FIG. 32 shows rhuMab C2B8 HCCF solubility curves—225 kDa polylysine

Similar trends were observed with rhuMab C2B8 HCCF (FIGS. 31 and 32). At 3 mS/cm and 6 mS/cm conductivities, both 50 kDa and 225 kDa polylysine resulted in 9 fold CHOP reduction. However no significant CHOP reduction was obtained at 12 mS/cm even with 225 kDa polylysine. This indicates that CHOP precipitation at high conductivities requires a highly charged polyelectrolyte like polyarginine to overcome the ionic interference. Yields were greater than 90% for all conditions tested.

Solubility curves were generated for three antibodies (rhuMab 2H7, anti-CD22 and rhuMab C2B8) using polyarginine (FIGS. 20-25, 29-32). CHOP precipitation was a function of pKa, molecular weight and concentration of polyelectrolyte as well as the ionic strength of the solution. Antibody properties such as charge density and isoelectric point also may play a role in the separation of impurities from antibodies. Impurities such as CHOP and DNA are removed by manipulating polyelectrolyte concentration and ionic strength. Polyelectrolyte properties such as functional group, molecular weight, charge density and hydrophobicity may be varied. Polyarginine may be used as a flocculent in CCF or as impurity precipitant in HCCF. Precipitation is conductivity dependent. A 10-25 fold CHOP removal was obtained and DNA was undetectable (Table 9). Polyarginine did not negatively impact the binding capacity of the SPSFF and is compatible with antibody precipitation with anionic polyelectrolytes and cation exchanger resins. Addition of polyarginine to HCCF also has surprising and unexpected additional benefits including inhibition of antibody reduction, possibly by precipitating the reducing agent along with other impurities.

EXAMPLES

In order to illustrate the invention, the following examples are included. However, it is to be understood that these examples do not limit the invention and are only meant to suggest methods of practicing the invention. Persons skilled in the art will recognize that the exemplary methods, protocols, processes, reagents, and apparatuses described may be readily adapted to practice alternative methods of this invention are deemed to be within the scope of this invention.

Example 1

Protein A Chromatography

The protein A column used Prosep vA resin and was used to purify rhuMab 2H7 present in the HCCF. The column diameter was 2.5 cm and the bed height was 14 cm. The column was operated at a flow rate of 40 CV/h (column volumes per hour). The Prosep vA column was run in multiple cycles (2 cycles). After equilibration, HCCF was applied to the column, and rhuMab 2H7 was retained on the column. The column was then washed with equilibration buffer followed by wash buffer and then again by equilibration buffer. After these washes were complete, elution buffer was applied to the column. Pooling was initiated based on absorbance at 280 nm (0.5 OD) and terminated after 2 column volumes. Regeneration buffer was subsequently applied to the column. Buffer composition and phase durations are indicated in Table 10.

TABLE 10

Prosep vA buffer composition and phase durations

| Buffer | Buffer component | Phase Duration (CV) |
|---|---|---|
| Equilibration buffer | 25 mM Tris, 25 mM NaCl, 5 mM EDTA, pH 7.1 | 5 |
| Load | rhuMab 2H7 HCCF | to 14 g/L capacity |
| Wash 1 buffer | 25 mM Tris, 25 mM NaCl, 5 mM EDTA, pH 7.1 | 3 |
| Wash 2 buffer | 0.4 M Potassium Phosphate pH 7.0 | 4 |
| Wash 3 buffer | 25 mM Tris, 25 mM NaCl, 5 mM EDTA, pH 7.1 | 3 |
| Elution buffer | 0.1 M Acetic acid pH 2.9 | 4 |
| Regeneration buffer | 0.1 M phosphoric acid | 3 |
| Storage solution | 0.1 M Acetate, 2% benzyl alcohol, pH 5.0 | 5 (last cycle only) |

The harvested cell culture fluid (HCCF) derived from the recombinant host cells may be loaded on the equilibrated solid phase using a loading buffer which may be the same as the equilibration buffer. As the contaminated preparation flows through the solid phase, the protein is adsorbed to the immobilized Protein A and other contaminants (such as Chinese Hamster Ovary Proteins, CHOP, where the protein is produced in a CHO cell) may bind nonspecifically to the solid phase. The next step performed sequentially entails removing the contaminants bound to the solid phase, antibody and/or Protein A, by washing the solid phase in an intermediate wash step. After loading, the solid phase may be equilibrated with equilibration buffer before beginning the intermediate wash step. The intermediate wash buffer may comprise salt and a further compound, where the further compound is (a) detergent, e.g. polysorbate 20 or polysorbate 80); (b) solvent (e.g. hexylene glycol); and (c) polymer (e.g. PEG). The salt employed may be selected based on the protein of interest, but preferably is acetate (e.g. sodium acetate). The amounts of the salt and further compound in the composition are such that the combined amount elutes the contaminant(s), without substantially removing the protein of interest. Salt concentrations in such wash buffers may range from about 0.1 to about 2 M, or from about 0.2 M to about 0.6 M. Useful detergent concentrations are from about 0.01 to about 5%, or about 0.1 to 1%, or about 0.5%, e.g. where the detergent is polysorbate. Exemplary solvent concentrations are from about 1% to 40%, or about 5 to about 25%. Where the further compound is a polymer (e.g. PEG 400 or PEG 8000), the concentration thereof may, for example, be from about 1% to about 20%, preferably from about 5% to about 15%.

In another embodiment, the intermediate wash step involves the use of a highly concentrated buffer solution, e.g. a buffer at a concentration of greater than about 0.8 M, e.g. up to about 2 M, and preferably in the range from about 0.8 M to about 1.5 M, most preferably about 1 M. In this embodiment, the buffer is preferably a Tris buffer, such as Tris acetate. The pH of the intermediate wash buffer may be about 4 to about 8, or from about 4.5 to about 5.5, or about 5.0. In another embodiment, the pH is about 7.0. Following the intermediate wash step of the preceding paragraph, the protein of interest is recovered from the column. This is normally achieved using a suitable elution buffer. The protein may, for example, be eluted from the column using an elution buffer having a low pH, e.g. in the range from about 2 to about 5, and preferably in the range from about 2.5 to about 3.5. Examples of elution buffers for this purpose include citrate or acetate buffers. During the elution phase of the Protein A operation, any non-specifically bound CHOP may co-elute with the protein of interest, compromising the purity of the product pool. To remove CHOP before the elution phase, exemplify an intermediate wash step using tetramethylammonium chloride (TMAC) may be conducted to remove CHOP (U.S. Pat. Nos. 6,870,034; 6,127,526; 6,333,398).

Example 2

SPSFF Chromatography

The cation exchange column used SP Sepharose Fast Flow (SPSFF) resin in bind and elute mode with a gradient elution. The SPSFF column was operated at a flow rate of 150 cm/h. In all cases the bed height was 30 cm. When processing intermediate chromatography pools (Prosep vA and QSFF pools), a 0.66 cm i.d. column was used and the column was loaded to 40 g/L. When processing HCCF, a 0.6-2.2 cm diameter column was used and the column was loaded to 10-40 g/L. In all cases, the load was conditioned to pH 5.0 and a conductivity of about 5.5 mS/cm. Following the load, the column was then washed with equilibration buffer followed by wash buffer and then again by equilibration buffer. After these washes were complete, rhuMab 2H7 was eluted in a gradient from 50 mM acetate to 350 mM acetate over 15 column volumes. Pooling was initiated and terminated based on absorbance at 280 nm (0.5 OD). The column was regenerated and sanitized with 0.5 N sodium hydroxide and stored in 0.1 N sodium hydroxide. Buffer composition and phase durations are indicated in Table 11.

TABLE 11

SPSFF buffer composition and phase durations

| Step | Buffer | CVs |
|---|---|---|
| Equilibration | 50 mM Na Acetate pH 5.5 | 5 |
| Wash 1 | 50 mM Na Acetate pH 5.5 | 3 |
| Wash 2 | 25 mM MOPS pH 7.1 | 5 |
| Wash 3 | 50 mM Na Acetate pH 5.5 | 3 |
| Elution | A: 50 mM Na Acetate pH 5.5<br>B: 350 mM NA Acetate pH 5.5 | 15 |
| Sanitization | 0.5 M NaOH | 4 |
| Storage | 0.1 M NaOH | 3 |

Example 3

Anion Exchange Chromatography

The anion-exchange column used Q Sepharose Fast Flow (QSFF) resin and was operated in flow-through mode. The QSFF column was operated at a flow rate of 150 cm/h. The column diameter was 0.66 cm and the bed height was 20 cm. The column was equilibrated and loaded at pH 8.0. RhuMab 2H7 antibody flowed through the column, which was then washed with equilibration buffer. Pooling was initiated and terminated based on absorbance at 280 nm (0.5 OD). The column was regenerated and sanitized with 0.5 N sodium hydroxide and stored in 0.1 N sodium hydroxide. Buffer composition and phase durations are indicated in Table 12.

TABLE 12

QSFF buffer composition and phase durations

| Step | Buffer | CVs |
|---|---|---|
| Equilibration | 50 mM Tris, 50 mM Acetate pH 8.0 | 8 |
| Load | Conditioned pool from previous step | to 40 g/L capacity |
| Wash 1 | 50 mM Tris, 50 mM Acetate pH 8.0 | 5 |
| Sanitization | 0.5 M NaOH | 4 |
| Storage | 0.1 M NaOH | 3 |

Example 4a

Anionic Polyelectrolyte Purification

Antibody pools were adjusted to the pH and conductivities outlined in Table 13. HCCF was adjusted to pH 6 with 1M Acetic acid and conductivity 2.0 mS/cm with WFI (water for irrigation). PVS was added inline to the conditioned HCCF to reach a final concentration of 0.05% w/v over a period of 20 minutes. While mixing, PVS was added to the conditioned pool to the final concentrations outlined in Table 13. The PVS precipitated pool was centrifuged at 4000 rpm (4657 g) at 10° C. for 30 minutes using a Sorval R3-CB centrifuge. The supernatant was removed and the pellet was washed with 25 mM MOPS, pH 7.1. The pellet was re-suspended in 50 mM Tris, 50 mM Acetate, and pH 8.0 (about 6.5 mS/cm). The re-suspended pellet was subsequently processed across QSFF chromatography.

Example 4b

Cationic Polyelectrolyte Purification

Cell culture fluid (CCF) precipitation: Impurity precipitation was performed with polyarginine, molecular weight 110 kDa. Polyarginine was added to CCF in a bioreactor over period of 5 minutes to reach a final concentration of 0.075% w/v, while mixing at 100 rpm. The flocculated CCF was then centrifuged at 10000 g and sterile filtered through a 0.2 μm filter.

Harvested cell culture fluid (HCCF) precipitation: Polyarginine (poly-L-arginine) was added to HCCF in a bioreactor over a period of 5 minutes to reach a final concentration of 0.1% w/v, while mixing at 100 rpm. The precipitated HCCF was then centrifuged at 5000 g and sterile filtered through a 0.2 um filter. The filtered feedstock was processed through different purification processes.

TABLE 13

PVS precipitation conditions for 2H7

| Run | Pool pH (−) | Pool Conductivity (mS/cm) | PVS (%) | PVS (M) | Antibody (mg/ml) | Antibody (M) | mol PVS/mol Ab |
|---|---|---|---|---|---|---|---|
| HCCF-Pro A-PVS-QSFF | 7 | 0.74 | 0.0125 | $6.94 \times 10^{-8}$ | 0.67 | $4.46 \times 10^{-9}$ | 15.57 |
| HCCF-SP-PVS-QSFF | 7 | 0.76 | 0.0125 | $6.94 \times 10^{-8}$ | 0.13 | $8.67 \times 10^{-10}$ | 80.13 |
| HCCF-PVS-QSFF-SPSFF | 5 | 3.05 | 0.0125 | $6.94 \times 10^{-8}$ | 0.19 | $1.24 \times 10^{-9}$ | 56.09 |
| HCCF-PVS-QSFF-SPSFF | 7 | 0.68 | 0.0031 | $1.74 \times 10^{-8}$ | 0.04 | $2.74 \times 10^{-10}$ | 63.44 |

Example 5

Protein Concentration Determination

Antibody concentration in the pools were determined by absorbance at 280 nm (with absorbance at 320 nm subtracted to correct for light scattering), using an 8453 spectrophotometer with a 10 mm path length flow cell (Agilent). An extinction coefficient of 1.75 ml/(mg cm) was employed. Antibody concentration was calculated using the following equation:

$$mg/mL = \frac{A_{280} - A_{320}}{1.75} \times \text{dilution factor}$$

Example 6

Size Exclusion Chromatography

Size-exclusion chromatography was used to monitor the size heterogeneity of rhuMAb 2H7 under native conditions. The assay employed a TSK-GEL G3000SWXL column (7.8 mm×300 mm, Tosohaas) to separate aggregates, monomer, and fragments. The column was operated at a flow rate of 0.3 mL/min using a 0.20 M potassium phosphate, 0.25 M potassium chloride pH 6.2 running buffer. The column was operated at ambient temperature. Samples were diluted in running buffer and 20 μg was injected for each sample. Absorbance at 280 nm was used to monitor levels of aggregates, monomer and fragments.

Example 7

CHOP ELISA—Y:42

An enzyme-linked immunosorbent assay (ELISA) using goat anti-CHOP antibodies was used to determine CHOP concentrations in all of the pools. For the ELISA, affinity purified goat anti-CHOP antibodies were immobilized on microtiter plate wells. Dilutions of the pool samples were incubated in the wells, followed by incubation with peroxidase-conjugated goat anti-CHOP antibodies. The horseradish peroxidase enzymatic activity was quantified with o-phenylenediamine which produces a colorimetric signal. Samples were serially diluted in assay diluent so that the absorbance reading fell within the range of the assay (5-320 ng/ml).

Example 8

Protein A ELISA—Y:80

The level of Protein-A was determined by a sandwich Protein-A ELISA. Chicken anti-staphylococcal protein A antibodies were immobilized on microtiter plate wells. Samples were diluted to 0.2 mg/ml antibody and applied to the wells. Protein A, if present in the sample, bound the coat antibody. Bound protein A was detected with horseradish peroxidase conjugated anti-protein antibodies. Horseradish peroxidase enzymatic activity was quantified with o-phenylenediamine which produces a colorimetric signal.

Example 9

Insulin ELISA—Y:64

An ELISA using guinea pig anti-insulin polyclonal antibodies was used to determine insulin concentrations in all of the pools. For the ELISA, affinity purified anti-insulin antibodies were immobilized on microtiter plate wells. Dilutions of the pool samples were incubated in the wells, followed by incubation with horseradish peroxidase-conjugated guinea pig anti-insulin antibodies. The horseradish peroxidase enzymatic activity was quantified with tetramethyl benzidine. Samples were serially diluted in assay diluent so that the absorbance reading fell within the range of the assay (0.094-3.000 ng/mL).

Example 10

Gentamicin ELISA—Y: 81

A competitive ELISA was used to determine gentamicin concentrations in all of the pools. Goat polyclonal antibodies to gentamicin-BSA were immobilized on microtiter plate wells. Gentamicin competed with biotinylated-gentamicin for binding to the antibodies. The amount of bound biotin-labeled gentamicin was detected with the addition of horseradish peroxidase-streptavidin and o-phenylenediamine substrate. Samples were serially diluted in assay diluent so that the absorbance reading fell within the range of the assay (0.37-90 ng/ml).

Example 11

CHO DNA PCR Assay—Y:77

DNA was quantified by PCR amplification of CHO DNA. DNA from samples and controls were first extracted using Qiagen's Viral RNA Mini kit. The extracts and standard curve, along with PCR master mix containing primers and probe, were then loaded in a 96-well plate format onto a commercial sequence detection system (Applied Biosystems), where CHO DNA was quantified using real-time PCR. TaqMan® PCR employs primers and probe that are designed specific to the target CHO DNA sequence. Product amplification was measured using a fluorogenic probe, labeled with a reporter dye at the 5' terminus, which is suppressed by a quencher dye at the 3' terminus. Taq polymerase begins amplification of the target DNA and upon reaching the probe, its 5' nuclease activity displaces the probe, releasing the reporter dye. With the reporter dye no longer is in proximity to the quencher dye, the reporter fluoresces, and the increase in emission intensity is measured. Cycle numbers at which DNA has amplified past the threshold (Ct) are calculated for the standard curve, against which unknown sample concentrations are quantified.

Example 12 rhuMAb 2H7 Potency rhuMAb 2H7 Potency was determined using a complement dependent cytotoxicity (CDC) assay. This assay is based on measuring the ability of rhuMAb 2H7 to lyse WIL2-S cells in the presence of human complement.

Example 13

RNase A Inhibition Assay for PVS

PVS is a potent inhibitor of RNase A. The assay uses an RNA analog with a fluorescent label on one end and a quencher on the other. Once the RNA analog is cleaved by RNase A, the fluorescent label is released from the quencher, yielding emission. The presence of PVS will inhibit the RNase A activity, limiting fluorescent emission. The amount of PVS can then be determined by comparing the observed fluorescence from a test sample to a standard curve.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

We claim:

1. A method of purifying antibodies comprising:
   (a) adjusting the acidity or salt concentration of a mixture containing an antibody wherein the antibody is derived from a harvested cell culture fluid;
   (b) adding a negatively charged polyelectrolyte selected from polyvinylsulfonic acid, polyvinylsulfonate, and polystyrenesulfonic acid, a molecular weight of 1200 to 1,100,000 Da, and a concentration between 0.01% to 1.0% weight/volume in the mixture containing the antibody, whereby a protein-polyelectrolyte precipitate is formed;
   (c) separating the protein-polyelectrolyte precipitate from impurities selected from protein aggregates, protein fragments, host cell proteins, insulin, gentamicin, DNA, and leached protein A;
   (d) isolating the protein-polyelectrolyte precipitate;
   (e) resuspending the protein-polyelectrolyte precipitate in an aqueous solution; and
   (f) separating the polyelectrolyte from the purified antibody by anion-exchange chromatography of the resuspended protein-polyelectrolyte precipitate.

2. The method of claim 1 wherein the antibody is selected from a monoclonal antibody, an antibody fragment, and a fusion protein.

3. The method of claim 2 wherein the antibody is selected from an anti-CD20 antibody, an anti-DR5 antibody, and an anti-CMET antibody.

4. The method of claim 3 wherein the anti-CD20 antibody is 2H7.

5. The method of claim 1 wherein the harvested cell culture fluid is derived from a mammalian cell culture.

6. The method of claim 5 wherein the mammalian cell culture is a chinese hamster ovary cell culture.

7. The method of claim 1 wherein the harvested cell culture fluid is derived from a microbial fermentation.

8. The method of claim 7 wherein the microbial fermentation is an *E.coli* fermentation.

9. The method of claim 1 wherein the antibody is derived from the harvested cell culture fluid by immobilization of the antibody on a protein A adsorbent.

10. The method of claim 1 wherein the antibody is derived from the harvested cell culture fluid by cation exchange chromatography.

11. The method of claim 1 wherein more than one negatively charged polyelectrolyte is added to the mixture.

12. The method of claim 1 wherein the protein-polyelectrolyte precipitate is isolated by centrifugation.

13. The method of claim 1 wherein the protein-polyelectrolyte precipitate is isolated by filtration.

14. The method of claim 1 wherein the protein-polyelectrolyte precipitate is isolated by depth filtration on a depth filter.

15. The method of claim 14 wherein the protein-polyelectrolyte precipitate is resuspended with a single pass of resolubilization buffer or recirculating resolubilization buffer through the depth filter.

* * * * *